United States Patent [19]
Goldstein et al.

[11] Patent Number: 5,593,842
[45] Date of Patent: Jan. 14, 1997

[54] METHOD OF MEASURING THYMOPOIETIN PROTEINS IN PLASMA AND SERUM INCLUDING ACIDIFICATION OF THE PLASMA AND SERUM

[75] Inventors: Gideon Goldstein, 30 Dorison Dr., Short Hills, N.J. 07078; Michael D. Culler, Easton, Pa.

[73] Assignee: Gideon Goldstein, Short Hills, N.J.

[21] Appl. No.: 309,419

[22] Filed: Sep. 20, 1994

[51] Int. Cl.$^6$ .............................. G01N 33/53; G01N 1/00; G01N 1/18
[52] U.S. Cl. ........................ 435/7.1; 435/7.92; 435/962; 435/967; 435/975; 436/174; 436/175; 436/177; 436/178
[58] Field of Search ...................... 435/7.1, 7.92, 435/7.93, 7.94, 7.95, 961, 962, 967, 975; 436/518, 86, 87, 174, 175, 177, 176, 178, 804; 530/301

[56] References Cited

U.S. PATENT DOCUMENTS

| | | |
|---|---|---|
| 4,454,232 | 6/1984 | Breglio et al. .......................... 436/504 |
| 4,562,147 | 12/1985 | Joo . |
| 4,703,001 | 10/1987 | Vodian et al. . |

OTHER PUBLICATIONS

G. Sunshine et al, "Thymopoietin Enhances the Allogeneic Response and Cyclic GMP Levels of Mouse Peripheral, Thymus–Derived Lymphocytes", *J. Immunol.*, 120(5):1594–1599 (May 1978).

G. Goldstein, "Isolation of Bovine Thymin: a Polypeptide Hormone of the Thymus", *Nature*, 247(5435):11–14 (Jan. 4, 1974) [Goldstein I].

D. Schlesinger et al, "The Amino Acid Sequence of Thymopoietin II", *Cell*, 5:361–365 (Aug. 1975).

G. Goldstein et al, "Thymopoietin and Myasthenia Gravis: Neostigmine–Responsive Neuromuscular Block Produced in Mice by a Synthetic Peptide Fragment of Thymopoietin", *Lancet*, 2:256–262 (Aug. 1975) [Goldstein II].

R. Brown et al, "Immunoreactive Thymopoietin in the Mouse Central Nervous System", *Brain Research*, 381:237–243 (Aug. 1986).

J. Twomey et al, "Bioassay Determinations of Thymopoietin and Thymic Hormone Levels in Human Plasma", *Proc. Natl. Acad. Sci. USA*, 74:2541–2545 (Jun. 1977) [Twomey I].

V. Lewis et al, "Age, Thymic Involution, and Circulating Thymic Hormone Activity", *J. Clin. Endo, Metab.*, 47(1):145–150 (Jul. 1978).

J. Twomey et al, "An Inhibitor of Thymic Hormone Activity in Serum from Patients with Lymphoblastic Leukemia", *Am. J. Med.*, 68:377–380 (Mar. 1980) [Twomey II].

G. Goldstein, "Radioimmunoassay for Thymopoietin", *J. Immunol.*, 117:690–692 (Aug. 1976) [Goldstein III].

P. Lisi et al, "Improved Radioimmunoassay Technique for Measuring Serum Thymopoietin", *Clin. Chim. ACTA*, 107:111–119 (Oct. 1980).

A. Fuccello et al, "Immunoassay for Bovine Serum Thymopoietin: Discrimination from Splenin by Monoclonal Antibodies", *Arch. Biochem. Biophys.*, 228:292–298 (Jan. 1984).

G. Goldstein et al, "The Thymus and Experimental Pathology", *The Human Thymus*, Wm. Heineman Med. Books Ltd., London, pp. 86–139 (1969) [Goldstein IV].

G. Goldstein, "Thymitis and Myasthenia Gravis", *Lancet*, 2:1164–1167 (Nov. 1966) [Goldstein V].

L. May et al, "High Levels of Complexed Interleukin–6 in Human Blood", *J. Biol. Chem.*, 267(27):19698–19704 (Sep. 1992).

L. Krummen et al, "Identification and Characterization of Binding Proteins for Inhibin and Activin in Human Serum and Follicular Fluids", *Endocrinology*, 132(1):431–443 (Jan. 1993).

T. Audhya et al, "Isolation and Complete Amino Acid Sequence of Human Thymopoietin and Splenin", *Proc. Natl. Acad. Sci. USA*, 84:3545–3549 (Jun., 1987) [Audhya I].

T. Audhya et al, "Amino Acid Sequence of Thymopoietin Isolated from Skin", *Annals New York Acad. Sci.*, 548:233–240 (1988) [Audhya II].

D. Zevin–Sonkin et al, "Molecular Cloning of the Bovine Thymopoietin Gene and its Expression in Different Calf Tissues: Evidence for a Predominant Expression in Thymocytes", *Immunol. Lett.*, 31:301–310 (1992).

Batteger et al, J. of Immunological Methods, 55:297–307, 1982.

Voller et al. in "Alternative Immuno Assays" published 1985 by John Wely & Sons Ltd. pp. 77–86.

*Primary Examiner*—Marian C. Knode
*Assistant Examiner*—Patricia A. Duffy
*Attorney, Agent, or Firm*—Howson and Howson

[57] ABSTRACT

Method for accurately measuring thymopoietin (TP) in human serum or plasma by dissociating TP from protein complexes, releasing bound TP in a unbound form, extracting TP, preparing it for assay, and measuring TP levels in a suitable assay.

11 Claims, 15 Drawing Sheets

FIGURE 1A

DNA and Amino Acid Sequences of TP α

GTTCGTAGTT CGGCTCTGGG GTCTTTTGTG TCCGGGTCTG GCTTGGCTTT GTGTCCGCGA

GTTTTTGTTC CGCTCCGCAG CGCTCTTCCC GGGCAGGAGC CGTGAGGCTC GGAGGCGGCA

GCGCGGTCCC CGGCCAGGAG CAAGCGCGCC GGCGTGAGCG GCGGCGGCAA AGGCTGTGGG

```
                                     -1  +1
GAGGGGGCTT CGCAGATCCC CGAG ATG     CCG GAG TTC CTG GAA GAC CCC TCG
                           Met     Pro Glu Phe Leu Glu Asp Pro Ser
                           -1      +1                   5

GTC CTG ACA AAA GAC AAG TTG AAG AGT GAG TTG GTC GCC AAC AAT GTG
Val Leu Thr Lys Asp Lys Leu Lys Ser Glu Leu Val Ala Asn Asn Val
         10              15                  20

ACG CTG CCG GCC GGG GAG CAG CGC AAA GAC GTG TAC GTC CAG CTC TAC
Thr Leu Pro Ala Gly Glu Gln Arg Lys Asp Val Tyr Val Gln Leu Tyr
 25              30                  35                       40

CTG CAG CAC CTC ACG GCT CGC AAC CGG CCG CCG CTC CCC GCC GGC ACC
Leu Gln His Leu Thr Ala Arg Asn Arg Pro Pro Leu Pro Ala Gly Thr
                 45                  50                  55

AAC AGC AAG GGG CCC CCG GAC TTC TCC AGT GAC GAA GAG CGC GAG CCC
Asn Ser Lys Gly Pro Pro Asp Phe Ser Ser Asp Glu Glu Arg Glu Pro
             60                  65                  70

ACC CCG GTC CTC GGC TCT GGG GCC GCC GCC GCG GGC CGG AGC CGA GCA
Thr Pro Val Leu Gly Ser Gly Ala Ala Ala Ala Gly Arg Ser Arg Ala
         75                  80                  85

GCC GTC GGC AGG AAA GCC ACA AAA AAA ACT GAT AAA CCC AGA CAA GAA
Ala Val Gly Arg Lys Ala Thr Lys Lys Thr Asp Lys Pro Arg Gln Glu
         90                  95                 100

GAT AAA GAT GAT CTA GAT GTA ACA GAG CTC ACT AAT GAA GAT CTT TTG
Asp Lys Asp Asp Leu Asp Val Thr Glu Leu Thr Asn Glu Asp Leu Leu
105                 110                 115                 120

GAT CAG CTT GTG AAA TAC GGA GTG AAT CCT GGT CCT ATT GTG GGA ACA
Asp Gln Leu Val Lys Tyr Gly Val Asn Pro Gly Pro Ile Val Gly Thr
                125                 130                 135

ACC AGG AAG CTA TAT GAG AAA AAG CTT TTG AAA CTG AGG GAA CAA GGA
Thr Arg Lys Leu Tyr Glu Lys Lys Leu Leu Lys Leu Arg Glu Gln Gly
                140                 145                 150

ACA GAA TCA AGA TCT TCT ACT CCT CTG CCA ACA ATT TCT TCT TCA GCA
Thr Glu Ser Arg Ser Ser Thr Pro Leu Pro Thr Ile Ser Ser Ser Ala
        155                 160                 165
```

FIGURE 1B

```
GAA AAT ACA AGG CAG AAT GGA AGT AAT GAT TCT GAC AGA TAC AGT GAC
Glu Asn Thr Arg Gln Asn Gly Ser Asn Asp Ser Asp Arg Tyr Ser Asp
    170             175             180

AAT GAA GAA GGA AAG AAG AAA GAA CAC AAG AAA GTG AAG TCC ACT AGG
Asn Glu Glu Gly Lys Lys Lys Glu His Lys Lys Val Lys Ser Thr Arg
185      *           190             195                 200

GAT ATT GTT CCT TTT TCT GAA CTT GGA ACT ACT CCC TCT GGT GGT GGA
Asp Ile Val Pro Phe Ser Glu Leu Gly Thr Thr Pro Ser Gly Gly Gly
                205             210             215

TTT TTT CAG GGT ATT TCT TTT CCT GAA ATC TCC ACC CGT CCT CCT TTG
Phe Phe Gln Gly Ile Ser Phe Pro Glu Ile Ser Thr Arg Pro Pro Leu
            220             225             230

GGC AGT ACC GAA CTA CAG GCA GCT AAG AAA GTA CAT ACT TCT AAG GGA
Gly Ser Thr Glu Leu Gln Ala Ala Lys Lys Val His Thr Ser Lys Gly
        235             240             245

GAC CTA CCT AGG GAG CCT CTT GTT GCC ACA AAC TTG CCT GGC AGG GGA
Asp Leu Pro Arg Glu Pro Leu Val Ala Thr Asn Leu Pro Gly Arg Gly
    250             255             260

CAG TTG CAG AAG TTA GCC TCT GAA AGG AAT TTG TTT ATT TCA TGC AAG
Gln Leu Gln Lys Leu Ala Ser Glu Arg Asn Leu Phe Ile Ser Cys Lys
265             270             275             280

TCT AGC CAT GAT AGG TGT TTA GAG AAA AGT TCT TCG TCA TCT TCT CAG
Ser Ser His Asp Arg Cys Leu Glu Lys Ser Ser Ser Ser Ser Ser Gln
            285             290             295

CCT GAA CAC AGT GCC ATG TTG GTC TCT ACT GCA GCT TCT CCT TCA CTG
Pro Glu His Ser Ala Met Leu Val Ser Thr Ala Ala Ser Pro Ser Leu
        300             305             310

ATT AAA GAA ACC ACC ACT GGT TAC TAT AAA GAC ATA GTA GAA AAT ATT
Ile Lys Glu Thr Thr Thr Gly Tyr Tyr Lys Asp Ile Val Glu Asn Ile
    315             320             325

TGC GGT AGA GAG AAA AGT GGA ATT CAA CCA TTA TGT CCT GAG AGG TCC
Cys Gly Arg Glu Lys Ser Gly Ile Gln Pro Leu Cys Pro Glu Arg Ser
330             335             340

CAT ATT TCA GAT CAA TCG CCT CTC TCC AGT AAA AGG AAA GCA CTA GAA
His Ile Ser Asp Gln Ser Pro Leu Ser Ser Lys Arg Lys Ala Leu Glu
345             350             355             360

GAG TCT GAG AGC TCA CAA CTA ATT TCT CCG CCA CTT GCC CAG GCA ATC
Glu Ser Glu Ser Ser Gln Leu Ile Ser Pro Pro Leu Ala Gln Ala Ile
            365             370             375
```

FIGURE 1C

```
AGA GAT TAT GTC AAT TCT CTG TTG GTC CAG GGT GGG GTA GGT AGT TTG
Arg Asp Tyr Val Asn Ser Leu Leu Val Gln Gly Gly Val Gly Ser Leu
            380             385                 390

CCT GGA ACT TCT AAC TCT ATG CCC CCA CTG GAT GTA GAA AAC ATA CAG
Pro Gly Thr Ser Asn Ser Met Pro Pro Leu Asp Val Glu Asn Ile Gln
            395             400                 405

AAG AGA ATT GAT CAG TCT AAG TTT CAA GAA ACT GAA TTC CTG TCT CCT
Lys Arg Ile Asp Gln Ser Lys Phe Gln Glu Thr Glu Phe Leu Ser Pro
            410             415                 420

CCA AGA AAA GTC CCT AGA CTG AGT GAG AAG TCA GTG GAG GAA AGG GAT
Pro Arg Lys Val Pro Arg Leu Ser Glu Lys Ser Val Glu Glu Arg Asp
425             430             435                 440

TCA GGT TCC TTT GTG GCA TTT CAG AAC ATA CCT GGA TCC GAA CTG ATG
Ser Gly Ser Phe Val Ala Phe Gln Asn Ile Pro Gly Ser Glu Leu Met
            445             450                 455

TCT TCT TTT GCC AAA ACT GTT GTC TCT CAT TCA CTC ACT ACC TTA GGT
Ser Ser Phe Ala Lys Thr Val Val Ser His Ser Leu Thr Thr Leu Gly
            460             465                 470

CTA GAA GTG GCT AAG CAA TCA CAG CAT GAT AAA ATA GAT GCC TCA GAA
Leu Glu Val Ala Lys Gln Ser Gln His Asp Lys Ile Asp Ala Ser Glu
            475             480                 485

CTA TCT TTT CCC TTC CAT GAA TCT ATT TTA AAA GTA ATT GAA GAA GAA
Leu Ser Phe Pro Phe His Glu Ser Ile Leu Lys Val Ile Glu Glu Glu
            490             495                 500

TGG CAG CAA GTT GAC AGG CAG CTG CCT TCA CTG GCA TGC AAA TAT CCA
Trp Gln Gln Val Asp Arg Gln Leu Pro Ser Leu Ala Cys Lys Tyr Pro
505             510             515                 520

GTT TCT TCC AGG GAG GCA ACA CAG ATA TTA TCA GTT CCA AAA GTA GAT
Val Ser Ser Arg Glu Ala Thr Gln Ile Leu Ser Val Pro Lys Val Asp
            525             530                 535

GAT GAA ATC CTA GGG TTT ATT TCT GAA GCC ACT CCA CTA GGA GGT ATT
Asp Glu Ile Leu Gly Phe Ile Ser Glu Ala Thr Pro Leu Gly Gly Ile
            540             545                 550

CAA GCA GCC TCC ACT GAG TCT TGC AAT CAG CAG TTG GAC TTA GCA CTC
Gln Ala Ala Ser Thr Glu Ser Cys Asn Gln Gln Leu Asp Leu Ala Leu
            555             560                 565

TGT AGA GCA TAT GAA GCT GCA GCA TCA GCA TTG CAG ATT GCA ACT CAC
Cys Arg Ala Tyr Glu Ala Ala Ala Ser Ala Leu Gln Ile Ala Thr His
            570             575                 580
```

FIGURE 1D

```
                                                            G
ACT GCC TTT GTA GCT AAG GCT ATG CAG GCA GAC ATT AGT CAA GCT GCA
Thr Ala Phe Val Ala Lys Ala Met Gln Ala Asp Ile Ser Gln Ala Ala
585             590             595         Glu         600

CAG ATT CTT AGC TCA GAT CCT AGT CGT ACC CAC CAA GCG CTT GGG ATT
Gln Ile Leu Ser Ser Asp Pro Ser Arg Thr His Gln Ala Leu Gly Ile
                605             610              615

CTG AGC AAA ACA TAT GAT GCA GCC TCA TAT ATT TGT GAA GCT GCA TTT
Leu Ser Lys Thr Tyr Asp Ala Ala Ser Tyr Ile Cys Glu Ala Ala Phe
            620             625             630

GAT GAA GTG AAG ATG GCT GCC CAT ACC ATG GGA AAT GCC ACT GTA GGT
Asp Glu Val Lys Met Ala Ala His Thr Met Gly Asn Ala Thr Val Gly
            635             640             645

CGT CGA TAC CTC TGG CTG AAG GAT TGC AAA ATT AAT TTA GCT TCT AAG
Arg Arg Tyr Leu Trp Leu Lys Asp Cys Lys Ile Asn Leu Ala Ser Lys
            650             655             660

AAT AAG CTG GCT TCC ACT CCC TTT AAA GGT GGA ACA TTA TTT GGA GGA
Asn Lys Leu Ala Ser Thr Pro Phe Lys Gly Gly Thr Leu Phe Gly Gly
665             670             675             680

GAA GTA TGC AAA GTA ATT AAA AAG CGT GGA AAT AAA CAC TAGTAAAATT
Glu Val Cys Lys Val Ile Lys Lys Arg Gly Asn Lys His
                685             690

AAGGACAAAA AGACATCTAT CTTATCTTTC AGGTACTTTA TGCCAACATT TTCTTTTCTG

TTAAGGTTGT TTTAGTTTCC AGATAGGGCT AATTACAAAA TGTTAAGCTT CTACCCATCA

AATTACAGTA TAAAAGTAAT TGCCTGTGTA GAACTACTTG TCTTTTCTAA AGATTTGCGT

AGATAGGAAG CCTG
```

FIGURE 2A

DNA and Amino Acid Sequence of TP β

GGTTGGTGCG AGCTTCCAGC TTGGCCGCAG TTGGTTCGTA GTTCGGCTCT GGGGTCTTTT

GTGTCCGGGT CTGGCTTGGC TTTGTGTCCG CGAGTTTTTG TTCCGCTCCG CAGCGCTCTT

CCCGGGCAGG AGCCGTGAGG CTCGGAGGCG GCAGCGCGGT CCCCGGCCAG GAGCAAGCGC

GCCGGCGTGA GCGGCGGCGG CAAAGGCTGT GGGGAGGGGG CTTCGCAGAT CCCCGAG

```
 -1  +1
ATG  CCG GAG TTC CTG GAA GAC CCC TCG GTC CTG ACA AAA GAC AAG TTG
Met  Pro Glu Phe Leu Glu Asp Pro Ser Val Leu Thr Lys Asp Lys Leu
 -1  +1              5                   10                  15

AAG AGT GAG TTG GTC GCC AAC AAT GTG ACG CTG CCG GCC GGG GAG CAG
Lys Ser Glu Leu Val Ala Asn Asn Val Thr Leu Pro Ala Gly Glu Gln
             20                  25                  30

CGC AAA GAC GTG TAC GTC CAG CTC TAC CTG CAG CAC CTC ACG GCT CGC
Arg Lys Asp Val Tyr Val Gln Leu Tyr Leu Gln His Leu Thr Ala Arg
             35                  40                  45

AAC CGG CCG CCG CTC CCC GCC GGC ACC AAC AGC AAG GGG CCC CCG GAC
Asn Arg Pro Pro Leu Pro Ala Gly Thr Asn Ser Lys Gly Pro Pro Asp
         50                  55                  60

TTC TCC AGT GAC GAA GAG CGC GAG CCC ACC CCG GTC CTC GGC TCT GGG
Phe Ser Ser Asp Glu Glu Arg Glu Pro Thr Pro Val Leu Gly Ser Gly
         65                  70                  75

GCC GCC GCC GCG GGC CGG AGC CGA GCA GCC GTC GGC AGG AAA GCC ACA
Ala Ala Ala Ala Gly Arg Ser Arg Ala Ala Val Gly Arg Lys Ala Thr
 80                  85                  90                  95

AAA AAA ACT GAT AAA CCC AGA CAA GAA GAT AAA GAT GAT CTA GAT GTA
Lys Lys Thr Asp Lys Pro Arg Gln Glu Asp Lys Asp Asp Leu Asp Val
                 100                 105                 110

ACA GAG CTC ACT AAT GAA GAT CTT TTG GAT CAG CTT GTG AAA TAC GGA
Thr Glu Leu Thr Asn Glu Asp Leu Leu Asp Gln Leu Val Lys Tyr Gly
             115                 120                 125

GTG AAT CCT GGT CCT ATT GTG GGA ACA ACC AGG AAG CTA TAT GAG AAA
Val Asn Pro Gly Pro Ile Val Gly Thr Thr Arg Lys Leu Tyr Glu Lys
             130                 135                 140

AAG CTT TTG AAA CTG AGG GAA CAA GGA ACA GAA TCA AGA TCT TCT ACT
Lys Leu Leu Lys Leu Arg Glu Gln Gly Thr Glu Ser Arg Ser Ser Thr
             145                 150                 155
```

FIGURE 2B

```
CCT CTG CCA ACA ATT TCT TCT TCA GCA GAA AAT ACA AGG CAG AAT GGA
Pro Leu Pro Thr Ile Ser Ser Ser Ala Glu Asn Thr Arg Gln Asn Gly
160             165             170             175

AGT AAT GAT TCT GAC AGA TAC AGT GAC AAT GAA GAA GAC TCT AAA ATA
Ser Asn Asp Ser Asp Arg Tyr Ser Asp Asn Glu Glu Asp Ser Lys Ile
                180             185          *      190

GAG CTC AAG CTT GAG AAG AGA GAA CCA CTA AAG GGC AGA GCA AAG ACT
Glu Leu Lys Leu Glu Lys Arg Glu Pro Leu Lys Gly Arg Ala Lys Thr
            195             200             205

CCA GTA ACA CTC AAG CAA AGA AGA GTT GAG CAC AAT CAG AGC TAT TCT
Pro Val Thr Leu Lys Gln Arg Arg Val Glu His Asn Gln Ser Tyr Ser
        210             215             220

CAA GCT GGA ATA ACT GAG ACT GAA TGG ACA AGT GGA TCT TCA AAA GGC
Gln Ala Gly Ile Thr Glu Thr Glu Trp Thr Ser Gly Ser Ser Lys Gly
    225             230             235

GGA CCT CTG CAG GCA TTA ACT AGG GAA TCT ACA AGA GGG TCA AGA AGA
Gly Pro Leu Gln Ala Leu Thr Arg Glu Ser Thr Arg Gly Ser Arg Arg
240             245             250             255

ACT CCA AGG AAA AGG GTG GAA ACT TCA GAA CAT TTT CGT ATA GAT GGT
Thr Pro Arg Lys Arg Val Glu Thr Ser Glu His Phe Arg Ile Asp Gly
            260             265             270

CCA GTA ATT TCA GAG AGT ACT CCC ATA GCT GAA ACT ATA ATG GCT TCA
Pro Val Ile Ser Glu Ser Thr Pro Ile Ala Glu Thr Ile Met Ala Ser
        275             280             285

AGC AAC GAA TCC TTA GTT GTC AAT AGG GTG ACT GGA AAT TTC AAG CAT
Ser Asn Glu Ser Leu Val Val Asn Arg Val Thr Gly Asn Phe Lys His
        290             295             300

GCA TCT CCT ATT CTG CCA ATC ACT GAA TTC TCA GAC ATA CCC AGA AGA
Ala Ser Pro Ile Leu Pro Ile Thr Glu Phe Ser Asp Ile Pro Arg Arg
    305             310             315

GCA CCA AAG AAA CCA TTG ACA AGA GCT GAA GTG GGA GAA AAA ACA GAG
Ala Pro Lys Lys Pro Leu Thr Arg Ala Glu Val Gly Glu Lys Thr Glu
320             325             330             335

GAA AGA AGA GTA GAA AGG GAT ATT CTT AAG GAA ATG TTC CCC TAT GAA
Glu Arg Arg Val Glu Arg Asp Ile Leu Lys Glu Met Phe Pro Tyr Glu
            340             345             350

GCA TCT ACA CCA ACA GGA ATT AGT GCT AGT TGC CGC AGA CCA ATC AAA
Ala Ser Thr Pro Thr Gly Ile Ser Ala Ser Cys Arg Arg Pro Ile Lys
        355             360             365
```

FIGURE 2C

```
GGG GCT GCA GGC CGG CCA TTA GAA CTC AGT GAT TTC AGG ATG GAG GAG
Gly Ala Ala Gly Arg Pro Leu Glu Leu Ser Asp Phe Arg Met Glu Glu
        370                 375                 380

TCT TTT TCA TCT AAA TAT GTT CCT AAG TAT GTT CCC TTG GCA GAT GTC
Ser Phe Ser Ser Lys Tyr Val Pro Lys Tyr Val Pro Leu Ala Asp Val
    385                 390                 395

AAG TCA GAA AAG ACA AAA AAG GGA CGC TCC ATT CCC GTA TGG ATA AAA
Lys Ser Glu Lys Thr Lys Lys Gly Arg Ser Ile Pro Val Trp Ile Lys
400                 405                 410                 415

ATT TTG CTG TTT GTT GTT GTG GCA GTT TTT TTG TTT TTG GTC TAT CAA
Ile Leu Leu Phe Val Val Val Ala Val Phe Leu Phe Leu Val Tyr Gln
                420                 425                 430

GCT ATG GAA ACC AAC CAA GTA AAT CCC TTC TCT AAT TTT CTT CAT GTT
Ala Met Glu Thr Asn Gln Val Asn Pro Phe Ser Asn Phe Leu His Val
            435                 440                 445

GAC CCT AGA AAA TCC AAC TGAATGGTAT CTCTTTGGCA CGTTCAACTT
Asp Pro Arg Lys Ser Asn
            450

GGTCTCCTAT TTTCAATAAC TGTTGAAAAA CATTTGTGTA CACTTGTTGA CTCCAAGAAC

TAAAAATAAT GTGATTTCGC CTCAATAAAT GTAGTATTTC ATTGAAAAGC AAAC
```

FIGURE 3A

DNA and Amino Acid Sequences of TP γ

CCCTGCTACC AAGGCCCAGC TATGGCCCCA GGGTTGAAAA GTTATGAGGG TCAGGGGTCT

TTTGTGTCCG GGTCTGGCTT GGCTTTGTGT CCGCGAGTTT TTGTTCCGCT CCGCAGCGCT

CTTCCCGGGC AGGAGCCGTG AGGCTCGGAG GCGGCAGCGC GGTCCCCGGC CAGGAGCAAG

CGCGCCGGCG TGAGCGGCGG CGGCAAGGC TGTGGGGAGG GGGCTTCGCA GATCCCCGAG

| -1 | +1 | | | | | | | | | | | | | |
|---|---|---|---|---|---|---|---|---|---|---|---|---|---|---|
| ATG | CCG | GAG | TTC | CTG | GAA | GAC | CCC | TCG | GTC | CTG | ACA | AAA | GAC | AAG | TTG |
| Met | Pro | Glu | Phe | Leu | Glu | Asp | Pro | Ser | Val | Leu | Thr | Lys | Asp | Lys | Leu |
| -1 | +1 | | | 5 | | | | | | 10 | | | | | 15 |

AAG AGT GAG TTG GTC GCC AAC AAT GTG ACG CTG CCG GCC GGG GAG CAG
Lys Ser Glu Leu Val Ala Asn Asn Val Thr Leu Pro Ala Gly Glu Gln
                    20                  25                  30

CGC AAA GAC GTG TAC GTC CAG CTC TAC CTG CAG CAC CTC ACG GCT CGC
Arg Lys Asp Val Tyr Val Gln Leu Tyr Leu Gln His Leu Thr Ala Arg
                35                  40                  45

AAC CGG CCG CCG CTC CCC GCC GGC ACC AAC AGC AAG GGG CCC CCG GAC
Asn Arg Pro Pro Leu Pro Ala Gly Thr Asn Ser Lys Gly Pro Pro Asp
            50                  55                  60

TTC TCC AGT GAC GAA GAG CGC GAG CCC ACC CCG GTC CTC GGC TCT GGG
Phe Ser Ser Asp Glu Glu Arg Glu Pro Thr Pro Val Leu Gly Ser Gly
        65                  70                  75

GCC GCC GCC GCG GGC CGG AGC CGA GCA GCC GTC GGC AGG AAA GCC ACA
Ala Ala Ala Ala Gly Arg Ser Arg Ala Ala Val Gly Arg Lys Ala Thr
80                  85                  90                  95

AAA AAA ACT GAT AAA CCC AGA CAA GAA GAT AAA GAT GAT CTA GAT GTA
Lys Lys Thr Asp Lys Pro Arg Gln Glu Asp Lys Asp Asp Leu Asp Val
                100                 105                 110

ACA GAG CTC ACT AAT GAA GAT CTT TTG GAT CAG CTT GTG AAA TAC GGA
Thr Glu Leu Thr Asn Glu Asp Leu Leu Asp Gln Leu Val Lys Tyr Gly
            115                 120                 125

GTG AAT CCT GGT CCT ATT GTG GGA ACA ACC AGG AAG CTA TAT GAG AAA
Val Asn Pro Gly Pro Ile Val Gly Thr Thr Arg Lys Leu Tyr Glu Lys
        130                 135                 140

AAG CTT TTG AAA CTG AGG GAA CAA GGA ACA GAA TCA AGA TCT TCT ACT
Lys Leu Leu Lys Leu Arg Glu Gln Gly Thr Glu Ser Arg Ser Ser Thr
    145                 150                 155

FIGURE 3B

```
CCT CTG CCA ACA ATT TCT TCT TCA GCA GAA AAT ACA AGG CAG AAT GGA
Pro Leu Pro Thr Ile Ser Ser Ser Ala Glu Asn Thr Arg Gln Asn Gly
160             165                 170                 175

AGT AAT GAT TCT GAC AGA TAC AGT GAC AAT GAA GAA GAC TCT AAA ATA
Ser Asn Asp Ser Asp Arg Tyr Ser Asp Asn Glu Glu Asp Ser Lys Ile
                180                 185     *           190

GAG CTT AAG CTT GAG AAG AGA GAA CCA CTA AAG GGC AGA GCA AAG ACT
Glu Leu Lys Leu Glu Lys Arg Glu Pro Leu Lys Gly Arg Ala Lys Thr
            195                 200                 205

CCA GTA ACA CTC AAG CAA AGA AGA GTT GAG CAC AAT CAG GTG GGA GAA
Pro Val Thr Leu Lys Gln Arg Arg Val Glu His Asn Gln Val Gly Glu
        210                 215                 220

AAA ACA GAG GAA AGA AGA GTA GAA AGG GAT ATT CTT AAG GAA ATG TTC
Lys Thr Glu Glu Arg Arg Val Glu Arg Asp Ile Leu Lys Glu Met Phe
    225                 230                 235

CCC TAT GAA GCA TCT ACA CCA ACA GGA ATT AGT GCT AGT TGC CGC AGA
Pro Tyr Glu Ala Ser Thr Pro Thr Gly Ile Ser Ala Ser Cys Arg Arg
240                 245                 250                 255

CCA ATC AAA GGG GCT GCA GGC CGG CCA TTA GAA CTC AGT GAT TTC AGG
Pro Ile Lys Gly Ala Ala Gly Arg Pro Leu Glu Leu Ser Asp Phe Arg
                260                 265                 270

ATG GAG GAG TCT TTT TCA TCT AAA TAT GTT CCT AAG TAT GTT CCC TTG
Met Glu Glu Ser Phe Ser Ser Lys Tyr Val Pro Lys Tyr Val Pro Leu
            275                 280                 285

GCA GAT GTC AAG TCA GAA AAG ACA AAA AAG GGA CGC TCC ATT CCC GTA
Ala Asp Val Lys Ser Glu Lys Thr Lys Lys Gly Arg Ser Ile Pro Val
        290                 295                 300

TGG ATA AAA ATT TTG CTG TTT GTT GTT GTG GCA GTT TTT TTG TTT TTG
Trp Ile Lys Ile Leu Leu Phe Val Val Val Ala Val Phe Leu Phe Leu
    305                 310                 315

GTC TAT CAA GCT ATG GAA ACC AAC CAA GTA AAT CCC TTC TCT AAT TTT
Val Tyr Gln Ala Met Glu Thr Asn Gln Val Asn Pro Phe Ser Asn Phe
320                 325                 330                 335

CTT CAT GTT GAC CCT AGA AAA TCC AAC TGA ATGGTAT CTCTTTGGCA
Leu His Val Asp Pro Arg Lys Ser Asn
                340
```

CGTTCAACTT GGTCTCCTAT TTTCAATAAC TGTTGAAAAA CATTTGTGTA CACTTGTTGA

CTCCAAGAAC TAAAAATAAT GTGATTTCGC CTCAATAAAT GTAGTATTTC ATTGAAAAGC

FIGURE 3C

AAACAAAATA TATATAAATG GACTTCATTA AAATGTTTTT GAACTTTGGA CTAGTAGGAG

ATCACTTTGT GCCATATGAA TAATCTTTTT TAGCTCTGGA ACTTTTTGTA GGCTTTATTT

TTTTAATGTG GGCATCTTAT TTCATTTTTG AAAAAATGTA TATGTTTTTT GTGTATTTGG

GAAACGAAGG GTGAAACATG GTAGTATAAT GTGAAGCTAC ACATTTAAAT ACTTAGAATT

CTTACAGAAA AGATTTTAAG AATTATTCTC TGCTGAATAA AAACTGCAAA TATGTGAAAC

ATAATGAAAT TCAGTAAGAG GAAAAGTAAC TTGGTTGTAC TTTTTGTAAC TGCAACAAAG

TTTGATGGTG TTTATGAGGA AAAGTACAGC AATAATCTCT TCTGTAACCT TTATTAATAG

TAATGTTGTT GTAGCCCTAT CATACTCACT TTTTAAGACA CAGTATCATG AAAGTCCTAT

TTCAGTAAGA CCCATTTACA TACAGTAGAT TTTTAGCAGA GATCTTTTAG TGTAACATAC

ATATTTTAGA GAATTGTTGG CTAGCTGTAC ATGTTTTGAA AAGCTGTTTA GCTAGCTATA

AGGCTATAAT TGGAAATTTG TATTTTTTAT TTACAGCAAA ACATTTATTC AGTCATCCAG

TTTGCTACCA AAATATGTTT TAGATAAGTG TGTGTATGTT TGTTTAGAAG TTAGAAATTG

TAAACACTGG TCTTATGTTT CATTTGGATT CATTATTGCA TTGTCTTGTT ACCAGAAACA

AATTTTGCCG AGCTTTTTTT GCCCTATATT TCCCAGCATA ATTTGATTAG AAAGTACAAA

AAGGGCCGGG CGCGGTGGCT TACGCCTGTA ATCCCAGCAC TTTGGGAGGC CAGGCGGGT

GGATCACGAG GTCAGGAGAT CGGGACCATC CTGGCCAACA TGGTGAAACC CCGTCTCTAC

TAAAAAAAAA AAAAAAA

FIGURE 4

Amino Acid Sequence of Human Thymopoietin

Pro Glu Phe Leu Glu Asp Pro Ser Val Leu Thr Lys Asp Lys
 1           5                       10

Leu Lys Ser Glu Leu Val Ala Asn Asn Val Thr Leu Pro Ala
 15              20                  25

Gly Glu Gln Arg Lys Asp Val Tyr Val Gln Leu Tyr Leu Gln
     30              35                  40

His Leu Thr Ala Arg Asn Arg Pro Pro Leu
         45              50

METHOD OF MEASURING THYMOPOIETIN PROTEINS IN PLASMA AND SERUM INCLUDING ACIDIFICATION OF THE PLASMA AND SERUM

The present invention relates generally to a method of measuring thymopoietin proteins in human plasma and serum samples.

BACKGROUND OF THE INVENTION

The thymic hormone thymopoietin (TP) has been shown to play a regulatory role in immune, nervous, and endocrine functions and has been isolated from bovine and human thymus. For additional general information on TP, see, also, G. H. Sunshine et al, *J. Immunol.*, 120:1594–1599 (1978); G. Goldstein, *Nature*, 247:11–14 (1974); D. H. Schlesinger and G. Goldstein, *Cell*, 5:361–365 (1975); G. Goldstein et al., *Lancet* 2:256–262 (1975). TP has also been found to be present in brain extracts [R. H. Brown, et al., *Brain Research* 381:237–243 (1986)].

Prior art bioassays which attempted to measure TP have been reported to be cumbersome, inaccurate and unreliable [J. J. Twomey, et al., *Proc. Natl. Acad. Sci. USA*, 74:2541–2545 (1977); V. M. Lewis, et al., *J. Clin. Endo. Metab.* 47.:145–150 (1978); J. J. Twomey, et al., *Am. J. Med.* 68:377–380 (1980)]. Immunoassays are the preferred format for measuring peptides and proteins in plasma or serum, but prior attempts to develop immunoassays to measure TP have not yielded clinically useful techniques. For example, a displacement radioimmunoassay (RIA) for measuring bovine TP was developed that detected TP concentrations greater than 5 ng/mL in tissue extracts. However this RIA is incapable of measuring TP levels in serum [see, e.g., G. Goldstein, *J. Immunol.* 117:690–692 (1976)].

The sensitivity of the TP RIA was subsequently increased to 20 picograms (pg) [see, e.g., P. J. Lisi et al, *Clin. Chim. ACTA*, 107:111–119 (1980)] using "human serum-based standards" and rabbit antisera. However, this assay has not proved effective or reproducible in practice. In addition, the present inventors observed that 20 picogram sensitivity is too poor to detect human blood levels of TP.

A sandwich enzyme-linked immunoassay (ELISA) was later developed for bovine TP using a combination of polyclonal and monoclonal antibodies [A. Fuccello et al, *Arch. Biochem. Biophys.*, 228:292–298 (1984)]. Although the assay provided specificity in distinguishing bovine TP from bovine splenin, it proved ineffective in measuring serum TP in humans.

There is considerable interest in the medical community in measuring TP levels for several reasons. For example, it has been found that as the thymus involutes with age, thymic hormone levels decrease, which is believed to be related to increased susceptibility to disease in aging [G. Goldstein and I. R. Mackay, *The Human Thymus*, Wm. Heineman Med. Books Ltd., London (1969)]. Additionally, hypersecretion of TP has been implicated in myasthenia gravis [G. Goldstein, *Lancet*, 2:1164–1167 (1966)], as being involved in the impairment of transmission of signal from nerve to muscle. When this signal is interrupted, the result is generalized weakness.

Thus, an assay capable of accurately detecting levels of human thymopoietin in plasma and serum is not yet available.

In view of the clinical significance for TP, and the lack of current methods capable of accurately detecting total levels of these factors in both plasma and serum, there is a significant unmet need in the art for a reliable method of accurately measuring total levels of specific peptide factors in human plasma and serum.

SUMMARY OF THE INVENTION

In one aspect, the present invention provides a simple and a reliable diagnostic method for determining levels of thymopoietin proteins which are found in either an aggregated or complexed state or bound to another protein. This method is particularly adapted for use in serum and plasma of human origin.

This method involves treating the sample under conditions sufficient to dissociate a selected peptide or protein factor, e.g., TP from association in protein complexes without denaturing the TP itself. Subsequent steps in the method include extraction of the TP protein to remove it from any assay interfering substances or complexing protein(s) present in the plasma/serum sample. The sample is then prepared for assay, and the TP protein measured by a selected assay. The method of the invention thus improves conventional TP assays, permitting them to detect levels of TP below 20 picograms.

In still another aspect, the present invention provides a kit for use by clinical laboratories or physicians in detecting the presence and/or level of TP or TP proteins in a serum/plasma sample.

Other aspects and advantages of the present invention are described further in the following detailed description of preferred embodiments thereof.

BRIEF DESCRIPTION OF THE DRAWINGS

FIGS. 1A–1D illustrates the nucleic acid sequence [SEQ ID NO:1] and amino acid sequence [SEQ ID NO:2] of human TPα.

FIGS. 2A–2C illustrates the nucleic acid sequence [SEQ ID NO:3] and amino acid sequence [SEQ ID NO:4] of human TPβ.

FIGS. 3A–3C illustrates the nucleic acid [SEQ ID NO:5] and amino acid [SEQ ID NO:6] sequences of human TP γ.

FIG. 4 illustrates the sequence of synthetic human TP, amino acids 1–52 [SEQ ID NO:7].

DETAILED DESCRIPTION OF THE INVENTION

Figure 5:
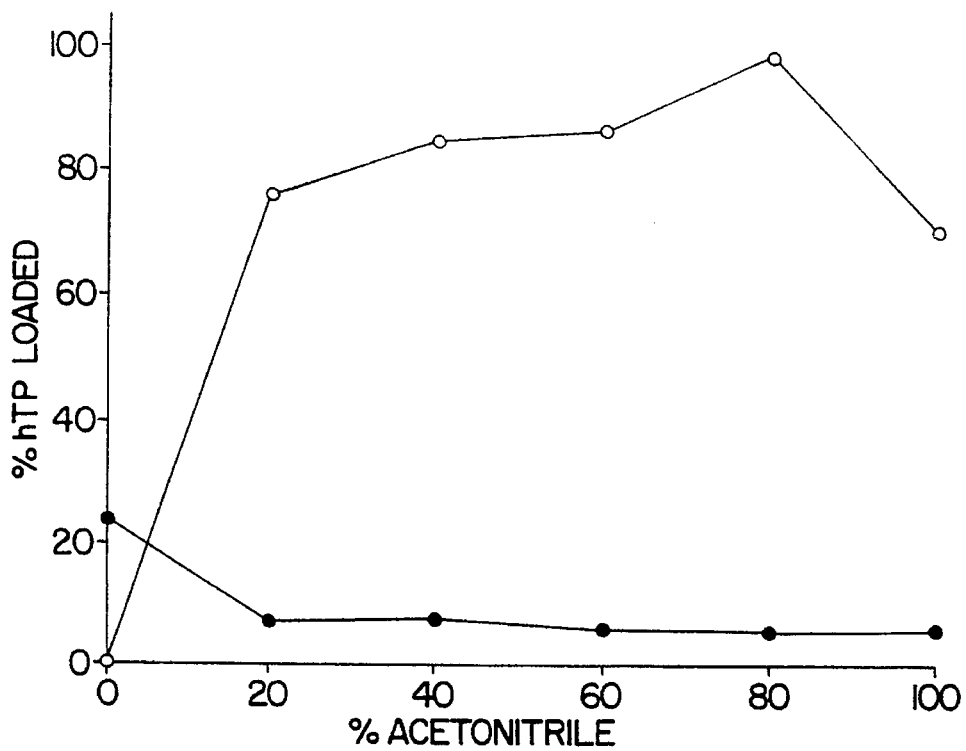
FIG. 5 is a graph illustrating the results following extraction and recovery of free TP from human plasma using C18, reverse phase cartridges, as described in Example 2 below. The solid circle (●) represents the percentage of hTP washed through and the open circle (o) represents the percentage hTP bound/recovered.

The present invention provides a method for measuring the total amounts of a TP protein in human serum or plasma. Advantageously, this invention provides a method of treating a human sample in preparation for assay, which permits a selected conventional assay to detect circulating TP levels and variances therein at TP levels below 20 picograms.

As used herein, the term "protein complex" includes agglomerations of thymopoietin with itself or with other related or unrelated protein forms, and peptides and proteins which complex with a specific complexing protein. The inventors have determined that TP, or selected TP forms, which are defined below, also form protein complexes which may include, in part or in whole, a binding protein. As used herein, human TP is defined as any of the three forms recently characterized by the recombinant TP protein sequences, TP$\alpha$, TP$\beta$ and TP$\gamma$ (FIGS. 1–3), as well as any other circulating proteins derived from these or other TP proteins.

The inventors have identified significant clinical interest in obtaining a suitable method for determining circulating TP levels, as well. Particularly, TP levels in serum have been observed to increase and decrease in relation to a variety of stimuli by bioassay. For example, decreases in total TP levels are believed to correlate with age and stress. TP levels may also be influenced by malnutrition, immunologically mediated diseases, cancer, and infections. Elevations in TP levels are also observed in other conditions, such as myasthenia gravis.

Briefly, the method of the present invention dissociates the TP from its association in any complexes that may have been formed by any naturally occurring binding proteins or other protein complexes in serum and plasma. This disassociation of complexes is performed without denaturing the TP which may naturally circulate in either a free and/or bound state, thus yielding the total TP in a free form for extraction and assay.

Following dissociation, the loss of free TP due to non-specific absorption onto equipment and vessels or re-complexing is prevented and the free TP extracted from any assay interfering substances present in the plasma/serum sample. After such extraction, any solvents or reagents that might be incompatible with the chosen assay method must be removed in preparing the TP sample for assay. The free TP is then measured using a suitable assay.

The method of the invention permits the measurement of total TP protein (e.g, any or all TP and TP forms circulating in a naturally unbound state plus all previously complexed TP).

A. Dissociation Step

According to one aspect of this method, the conditions for the first step, i.e., dissociating the TP from any complex, involves acidifying the serum or plasma sample sufficiently to effect the dissociation of bound TP from a protein complex. Generally, the sample is acidified with a selected acid to provide a sample pH of less than about 3. However, it is anticipated that partial and, eventually, complete dissociation may be achieved at other sample pH levels less than neutral.

A presently preferred acid for use in this acidification/extraction step is trifluoroacetic acid (TFA). It is contemplated that, in addition to TFA, other acids, and pH adjusting reagents known to those of skill in the art may be employed in the acidification step and subsequent steps of this method. Other acids which may be substituted for TFA include, without limitation, mineral acids, such as hydrochloric, nitric and sulfuric acid. Suitable acidic conditions may be adjusted conventionally by one of skill in the art in response to the substitution of the acid described as the presently preferred example herein.

Generally, the serum or plasma sample is diluted at a ratio of about 1:16 with about 0.1% trifluoroacetic acid (TFA) containing about 0.01% polyoxethylene-sorbitan monolaurate (Tween® 20) and allowed to incubate at room temperature for about 1 hour. Dilution of sample is not necessary for dissociation of TP from its protein complex or binding protein, but is convenient for introducing the dissociated sample into the presently preferred extraction method. The plasma/serum to acid solution ratio employed for the TFA may also be employed with other selected acids of similar strength to obtain the desired pH. Alternatively, for acids of greater or lesser strength, or for reasons of compatibility with subsequent extraction and assay methods, this ratio may be adjusted appropriately by one of skill in the art.

The incubation period of about one hour allows complete dissociation of TP from binding proteins or protein complexes to occur. It is also contemplated that, as an alternative to the one hour incubation step at room temperature, other incubation times and temperatures utilized by those of skill in the art may be employed to achieve dissociation of TP from circulating proteins or protein complexes under acidified conditions. Suitable time and temperature conditions to achieve dissociation of bound TP from any protein complexes may be adjusted by one of skill in the art as desired following, for example, the substitution of one or more dissociation reagents, requirements for subsequent extraction or assay methods, restraints of available equipment, supplies, or time or for sake of convenience.

Tween® 20 reagent (polyoxyethylenesorbitan monolaurate) is added to the acid solution to prevent the loss of free TP to non-specific binding of the TP to the dissociation and extraction vessels and other equipment. As an alternative to Tween® 20 reagent, other surfactants, detergents, and non-specific binding reducing reagents known to those of skill in the art may be employed to prevent such non-specific binding. Other agents which might be substituted for the Tween® 20 reagent include, without limitation, other detergents of the nonionic polyoxyethylene ether type, identified by the trademarks such as Triton® X, Lubrol® PX and NP40®, or detergents of the zwitterion type, such as 3-[(3-cholamidopropyl)-dimethylammonio]-1-propanesulfonate (CHAPS). When another non-specific binding reducing reagent is substituted for the Tween® 20 reagent, the conditions for preventing loss of free TP may be adjusted by one of skill in the art accordingly. For agents of greater or lesser non-specific binding blocking ability or for reasons of compatibility with subsequent extraction and assay methods, the concentration of 0.01% may be adjusted by one of skill in the art. For example, for an agent with a greater binding blocking ability than Tween® 20 reagent, the concentration of 0.01% may be decreased.

As an alternative to acidification, the method of dissociation of free TP from any protein complex or binding protein may be accomplished by other dissociation reagents known to those of skill in the art. These reagents include, without limitation, sodium iodide, high salt concentrations such as sodium chloride or potassium chloride, cyanide, guanidine hydrochloride, urea, etc.

Under the described conditions, the TP is dissociated from its binding protein or protein complex.

B. Extraction Step

Once the TP is so dissociated, it may be extracted from the sample in order to prevent reaggregation that may potentially interfere with subsequent assay of TP content.

A presently preferred method for the extraction of free TP is through the use of a C-18 reverse phase cartridge. The C-18 packing is believed to provide a non-polar, hydrophobic matrix. When materials carried in an aqueous, polar solvent are introduced into the C-18 matrix, the material of lesser polarity than the solvent and/or of a less hydrophilic nature will be driven into and bind to the C-18 matrix. The cartridge is then washed thoroughly with the aqueous buffer in order to remove all unbound materials.

Experimental results have established that free TP will bind to activated C-18 matrix while TP assay-interfering plasma substances will not. The materials bound to the cartridge matrix can then be eluted by the use of solvents of lower polarity and/or a less hydrophilic nature. Such alterations in the solvent nature are attained through the mixing of lower polarity, more hydrophobic organic solvents with the aqueous solvent.

The presently preferred method utilizes C-18 SepPak® cartridges (™Waters, a Division of the Millipore Corp.). The SepPak® cartridge is activated by the sequential passage through the cartridge of deionized, distilled water, a 20:80 ratio of 0.1% TFA:acetonitrile for TP extraction, and 0.1% TFA alone in sufficient quantities to achieve full activation. For the presently preferred cartridge size of 2 g C-18 matrix, the volume of each reagent used for activation is 40 ml. The dissociated sample in the 1:16 ratio with 0.1% TFA containing 0.01% Tween® 20 reagent is passed completely through the cartridge followed by a wash of the cartridge with 0.1% TFA containing 0.01% Tween® 20 reagent to remove all unbound material including any complexing protein now separated from the TP. The presently preferred wash volume is 20 ml followed by the passage of air to ensure removal of all solvent from the cartridge.

Desirably, the free TP, now bound to the C-18 matrix, is eluted with an appropriate ratio of TFA:acetonitrile containing 0.01% Tween® 20 reagent. The presently preferred elution volume is 10 ml followed by the passage of air to ensure removal of all solvent from the cartridge. The eluted, free TP, is then contained in the mixture of 0.1% TFA:acetonitrile containing 0.01% Tween® 20 reagent. The elution is preferably performed using a 20:80 ratio of 0.1% TFA:acetonitrile and the eluted, free TP is contained in the 20:80 mixture.

Other conditions known to those of skill in the art may be employed with C-18, reverse phase cartridges to produce comparable results in separating the TP from substances that might potentially interfere with the assay. For example, conditions that may be altered include, without limitation, the volumes of reagents employed for cartridge activation, sample loading, washing and elution, the volume and dilution factor of the plasma/serum sample prior to extraction, the reagents utilized for activation, sample loading, washing and elution, the ratio of aqueous phase reagent and organic phase reagent required to activate the C-18 matrix and elute the TP, the order of solvent application to the cartridge, the reagent utilized to minimize non-specific binding of the TP to the extraction equipment, the source and size of the C-18 cartridges, the method for passing the materials through the cartridge. The extent to which any of these parameters may be altered may be readily determined by one of skill in the art.

Other methods to extract free TP from potentially interfering plasma substances may include without limitation, high-performance liquid chromatography (HPLC), size-exclusion chromatography, ion exchange chromatography, dye-ligand chromatography, affinity chromatography, lectin-carbohydrate binding matrixes, solvent extractions, ultrafiltration, dialysis, etc.

C. Sample Preparation

The TFA and acetonitrile present in the sample following the extraction step described above must be separated from the TP prior to assay in order to prevent interference of these solvents with the assay reagents. The presently preferred method of removing acetonitrile is to evaporate the eluted solvent in a heated block (about 40° C.) under a stream of nitrogen gas. The evaporation is preferably performed to at least about 20% of the original, eluted volume. The remaining aqueous TFA solution is removed by freezing with subsequent lyophilization. The volatile TFA is removed during the sublimation process of lyophilization.

Certain assay systems may be sensitive to the residual TFA in the sample following lyophilization. For these types of assay systems, experimental results have demonstrated that TFA can be additionally removed from the sample prior to elution from the SepPak® cartridge by washing the SepPak® cartridge with distilled, deionized water containing 0.01% Tween® 20 reagent following the 0.1% TFA wash step to remove the unbound binding protein. The free TP is then eluted from the SepPak® cartridge with an appropriate ratio of distilled, deionized water:acetonitrile containing 0.01% Tween® 20 reagent. The acetonitrile is then evaporated from the sample and the remaining aqueous phase lyophilized as before.

Other conditions known to those of skill may be employed to prepare the extracted TP for assay. For example, the use of different gases to remove the organic phase, the method of removing the organic solvent from the eluted sample, the method of removing any material that may interfere with subsequent steps from the aqueous phase and the method of rendering of the free TP suitable for assay following extraction if a different extraction method is used.

D. Assay

The free TP now substantially free of protein complexes, and interfering materials, e.g., solvents and reagents used for extraction, are placed into a medium suitable for use in the assay of choice. With the presently preferred methodology for extraction and solvent removal, the final sample is in a dry state. Thus, placing the sample into the appropriate assay medium involves resuspending the sample in the medium of choice, mixing, and centrifuging the sample to remove any denatured protein that may have formed as a result of the extraction process.

The presently preferred assay medium is 0.05 M phosphate buffered physiologic saline (PBS) containing 0.025 M ethylenediaminetetraacetic acid (EDTA), 0.04% sodium azide, 1% bovine serum albumin, and 0.1% Tween® 20 reagent. Alternatively, other media known to those of skill in the art may be employed. Examples of other assay media include, without limitation, borate buffer, citrate buffer, HEPES buffer, succinate buffer, and defined cell culture and growth media. Other methods of medium transfer known to those of skill in the art may be employed depending on the final state of the sample following extraction and solvent removal. Examples of other medium transfer methods include, without limitation, dialysis, ultrafiltration and column chromatography exchange.

The extracted plasma/serum sample now suspended in an appropriate assay medium can be assayed for the mass of total TP, a specific TP form (e.g. α, β, or γ), or a circulating TP molecule derived from one of these proteins. The presently preferred method of quantitating TP is the use of an enzyme-linked immunoassay. However, other appropriate assay methods may be selected, e.g. fluorescence assays such as those employing europium, electrophoretic methods, receptor assays, bioassays, and mass spectroscopy.

These assays may use a variety of conventional indicator molecules which are known to those of skill in the art, including radioisotopes, colorimetric enzyme systems and the like. For example, $^{125}$I-TP, $^{3}$H-TP, horseradish peroxidase (HRP), enzyme-linked biotin-avidin, and fluorescein-antifluorescein systems, among others, may be employed. The particular assay format or indicator molecule used to measure the total TP is not necessarily critical to the performance of this method. Each assay method must be individually assessed for its appropriateness in quantitating TP in the plasma/serum extract.

One particularly desirable and sensitive assay for the measurement of TP in the serum/plasma extract is enzyme-linked "sandwich" immunoassay (ELISA). This assay method offers the advantages of specificity for TP, a high degree of sensitivity and precision, and the ability to selectively measure total TP or individual TP forms (e.g. α [SEQ ID NO:2], β [SEQ ID NO:4] or γ [SEQ ID NO:7]). The application of ELISA to quantitate total TP, or an individual TP form, defined above, obtained by the method of this invention, permits the ELISA to be characterized by a dilution curve of sample that is parallel to the standard curve. Although ELISA is the presently preferred assay method for TP, other methods known to those of skill in the art may be employed to quantitate TP in the extracted sample.

The standard preparation for TP in such an assay may be recombinantly produced human TP α, β, or γ or recombinantly or synthetically produced peptides corresponding to α, β or γTP, or fragments thereof. Suitable fragments include those encompassing one or more selected TP epitopes, e.g. amino acids 1–19 and amino acids 29–50 of α,β,γ [SEQ ID NO:2, 4, 6]. To measure total TP, it is preferable to utilize a form of TP that contains epitopes common to all TP forms and that are utilized by the assay for recognition, such as amino acids 1–52 of α,β,γ [SEQ ID NO: 2, 4, 6].

Although recombinant TP forms or specific synthetic regions of TP, e.g. TP 1–52 [SEQ ID NO:7], are the presently preferred standard for the assay, other TP molecules and sequences known to those of skill in the art may be employed as standards. These alternative standard preparations include, without limitation, recombinantly produced TP sequence fragments, synthetic fragments of α, β, and γ [SEQ ID NO:2, 4, 6], and any other circulating proteins derived from these or other TP proteins. As one example, synthetic TP amino acids (AA) 1–52 can be utilized as a common standard for TPα, TPβ, and TPγ [SEQ ID NO:2, 4, 6], which were all isolated from a human cDNA library (see FIGS. 1–4).

The assays employed to measure the TP may also employ anti-TP polyclonal, monoclonal or recombinant antibodies. Polyclonal antibodies to TP may be generated by conventional methods. For example, see the high titer anti-human/rat TP antibody of Example 3.

Monoclonal antibodies (MAbs) with increased target specificity may also be used in the assays of this invention. Additionally, synthetically designed monoclonal antibodies may be made by known genetic engineering techniques and employed in the methods described herein. For use in the assays any MAb generated by the techniques of Kohler and Milstein [*Nature*, 256:495 (1975)] and modifications thereof and directed to an epitope on TP may be employed. However, the assays useful in this invention are not limited to the use of specific polyclonal antibodies or MAbs, since other antibodies may be generated by one of skill in the art to appropriate epitopes of TP.

The choice of monoclonal antibodies or polyclonal antiserum for use in the ELISA or immunoassay of choice confers to the assay specificity for total TP, a certain subclass of TP, or individual TP forms. For example, antisera generated against the AA 1–19 portion of the TP molecule that is common to TPα, TPβ, and TPγ [SEQ ID NO:2,4,6] would be expected to recognize these molecules, as well as any TP α, β, γ derivatives that contained the AA 1–19 sequence. For instance, in an ELISA assay, using the AA 1–19 antiserum to coat a well would mean that subsequent exposure of the coated well to extracted plasma or serum would allow capture of any and all molecules present in the extract that contained the AA 1–19 sequence [SEQ ID NO:2,4,6]. The specificity of the assay with regard to the classification of the TP to be measured is determined by the detecting antibody or antisera specificity selected. For example, utilizing an enzyme coupled detecting antibody specific to the AA 29–50 portion of the TP molecule that is common to TPα, TPβ, and TPγ [SEQ ID NO:2,4,6] allows detection and quantitation of total TP in the sample, whereas the use of an enzyme coupled detecting antibody generated against a β-specific region of the β-TP molecule would allow detection and quantitation of only the β-TP molecules present. The choice of antisera/antibodies utilized in the ELISA or other immunoassay to quantitate TP can be determined by one skilled in the art to render the assay specific for the particular class of TP molecules to be quantitated.

The methods and assay components described L0 herein for the collection and measurement of TP in serum or plasma may be efficiently utilized for the routine measurement of TP in human clinical samples as a diagnostic test for pathologies and physiologic states in which TP levels may be altered either directly or indirectly as an indicator of dysfunction. For example, use of methods of the present invention enables diagnosis of conditions characterized by imbalances in TP levels. These conditions may include, for example, HIV infection, myasthenia gravis, immune system disorders, and other physiological disorders.

In addition, these methods may be utilized for the effective measurement of TP in clinical studies of TP physiology, pharmacology and pathology or as a direct or indirect index of changes induced by other drugs or biologically active reagents. These methods may also be effectively utilized to follow the distribution and pharmokinetics of a selected TP and related analogues in human clinical studies and trials.

In another embodiment, the present invention provides a diagnostic kit which may be used in a clinical laboratory to aid in the diagnosis or assessment of the hormonal and immunological status of patients. The methods and assay components described herein for the collection and measurement of the TP in serum or plasma may be efficiently utilized in the assembly of such a kit for the detection of total TP in a serum or plasma sample. Thus, the kit may contain an appropriate binding ligand capable of binding the TP, an appropriate standard and controls, an appropriate assay indicator molecule, appropriate amounts of acid and organic solvent for extraction of TP, C-18 reverse phase cartridges, and assay buffer. Such an appropriate binding ligand may be selected by one of skill in the art and may be, for example, an antibody, a receptor, or other conventional ligand. This kit may be employed for the performance of one or more methods of this invention. Components of the kit may vary according to the utilized dissociation reagents, extraction method and assay method as discussed.

Advantageously, use of such a kit, and the method of the invention provides an accurate method for measuring total TP in serum or plasma, resulting in displacement curves parallel to the standard. These parallel curves permit the accurate measurement of total TP levels by comparison to the standard.

The following examples are presented to illustrate the invention without specifically limiting the invention thereto.

EXAMPLE 1

Synthesis of the Linear Peptides TP 1–52

The linear peptide of the hTP sequence of SEQ ID NO:7 (FIG. 4), $HTP_{1-52}$, was synthesized on an Applied Biosystems Model 430A peptide synthesizer using the solid-phase method developed by Merrifield, cited above. Peptide assembly was carried out starting with the appropriate t-butyloxycaronyl(Boc)-protected amino acid phenylacetomidomethyl (PAM)-resin and the Boc-protected amino acids using a symmetrical anhydride activation procedure. All the amino acids were double coupled to ensure complete coupling. Side chain protecting groups were as follows: benzyl ether for the hydroxyl group of threonine and serine; benzyl ester for the carboxyl group of aspartic and glutamic acids; tosyl for the guanidine of arginine; benzyloxymethyl for the imidazole of histidine; 2-chlorobenzyloxycarbonyl for the ε-amine of lysine; 2-bromobenzyloxycarbonyl for the phenolic hydroxyl of tyrosine. Asparagine, glutamine and arginine were coupled as their 1-hydroxylbenzotriazole esters. The following abbreviations are used in the examples below: Bzl is benzyl, Z is phenylmethoxycarbonzyl, TCA is trichloroacetic acid and BHA is benzhydrylamine resin.

This synthetic TP AA 1–52 is illustrated in FIG. 4 and is used in the examples below.

EXAMPLE 2

Demonstration of Recovery of Free TP 1–52 from C-18 Reverse Phase Cartridge

To demonstrate the ability of SepPak® C-18, reverse phase cartridges to bind free TP and to release the free TP under the proper eluting conditions, $^{125}I$-labeled TP AA 1–52 [SEQ ID NO:7], prepared by the method of Culler et al, *Proc. Soc. Exp. Biol. Med.*, 173:264–268 (1983) was added to a sample of human plasma, incubated for 15 min at 37° C. in order to allow interaction with any endogenous TP complexing proteins, acidified and allowed to incubate at room temperature for 1 hour to achieve dissociation and loaded onto an activated SepPak® C-18, reverse phase cartridge. Prior to dissociation, the plasma sample was counted in a gamma counter to determine the amount of $^{125}I$-labeled TP 1–52 present in the sample. To achieve dissociation, the sample had been acidified by dilution at a ratio of about 1:16 in 0.1% trifluoroacetic acid containing 0.01% Tween® 20 reagent to prevent non-specific absorption of free TP onto laboratory vessels and equipment. The SepPak® cartridge had been activated through the sequential passage of distilled, deionized water, 0.1% TFA:acetonitrile at ratios of 100:0, 80:20, 60:40, 40:60, 20:80 and 0:100, depending on the final eluting ratio, and, finally, 0.1% TFA alone. The dissociated sample was passed through the SepPak® cartridges and the material passing through the cartridges was collected. Each cartridge was then washed with 0.1% TFA containing 0.01% Tween® 20 reagent to completely remove all unbound material. Air was then passed through the cartridge to completely push all of the wash solution through the cartridge. The bound TP was eluted with the appropriate ratio of 0.1% TFA:acetonitrile, depending on the ratio used to initially condition the column. The eluting solvents contained 0.01% Tween. Air was then passed through the cartridge to completely push all of the eluting solution through the cartridge. The eluting material was collected and saved. The collected fractions were then counted in a gamma counter in order to determine the amount of radioactivity present in each and, thereby, the distribution of the free TP in the various materials passed through the column.

As illustrated in FIG. 5, over 95% of the $^{125}I$-labeled TP 1–52 originally added to the plasma sample was present in the material eluted from the cartridge with the 20:80 ratio of 0.1% TFA:acetonitrile. These results indicate that the free TP was separated from the sample and bound to the cartridge during the initial sample passage, was held onto the cartridge during the subsequent washing step and most fully eluted with 20:80 0.1% TFA:acetonitrile.

EXAMPLE 3

Preparation of high-titer polyclonal rabbit anti-TP antiserum

The following rapid, multi-site, multi-route hyperimmunization protocol was used. A multiple antigen peptide (MAP) consisting of AA 1–19 of the synthetic TP [SEQ ID NO:7] attached to a poly-Lys core octomer ($hTP_{(1-19)}$ octomeric MAP) was prepared essentially as described in J. P. Tam, *Vaccines Research and Development*, Vol. 1, ed. W. Koff and H. Six, Marcel Dekker, Inc., New York, N.Y. (1992), pp. 51–87. On days 1 and 5, 100 µg of the $hTP_{(1-19)}$ octomeric MAP dissolved in phosphate buffer saline (PBS) was injected intravenously (i.v.) and intraperitoneally (i.p.), respectively; 200 µg of the polypeptide emulsified in Freund's Incomplete adjuvant (Sigma Chemical Company) was injected subcutaneously (s.c.) at six different sites. On day 11, 100 and 500 µg of the polypeptide was injected i.v. and i.p. respectively, and 100 µg incomplete Freund's adjuvant was given s.c. On day 18, 500 µg of polypeptide in PBS was given i.p. and 500 µg incomplete adjuvant was given s.c. On days 24 and 31, 500 µg of the polypeptide without adjuvant was administered i.p. and s.c. On day 38 and at 3- to 6-week intervals thereafter, the rabbits were boosted with 200 µg of nonadjuvanted polypeptide in PBS administered subcutaneously.

Rabbits were bled on day 44, and 7 to 14 days after each boost. The antiserum was titrated by ELISA on $HTP_{(1-19)}$ octomeric MAP-coated Immulon 4® polystyrene microtiter plates (Dynatech Labs, Inc., Chantilly, Va.), and also on ovalbumin coated plates (Sigma Chemical Company) to determine the nonspecific binding as follows.

Rabbit anti-HTP$_{(1-19)}$ was diluted 1:5,000 in PBS/Tween-20 and 0.5% BSA (RIA grade). From this initial dilution, serial dilutions were made. One hundred (100) μL per well of each dilution of rabbit anti-HTP$_{(1-19)}$ was plated in triplicate on an HTP$_{(1-19)}$ octameric MAP-coated or ovalbumin-coated Immulon 4 microtiter plate. The plates were incubated for two hours at 37° with rocking. Plates were then washed five times with PBS/Tween® 20 reagent. Goat anti-rabbit IgG/HRPO [Antibodies Inc.] was added (100 μL/well) at the appropriate concentration in PBS/Tween® 20 reagent and 0.5% BSA. The plates were again incubated at 37° C. for one hour. Following this second incubation, the plates were washed five times with PBS/Tween® 20 reagent. TM Blue® reagent (Transgenic Sciences, Inc., Milford Mass.) was added (100 μL/well) and incubated in the dark with gentle rocking for 30 minutes (room temperature). The reaction was terminated by adding 2.5 N HCl (50 μL) to each well and the plate was read immediately at 450 nM.

Figure 6:
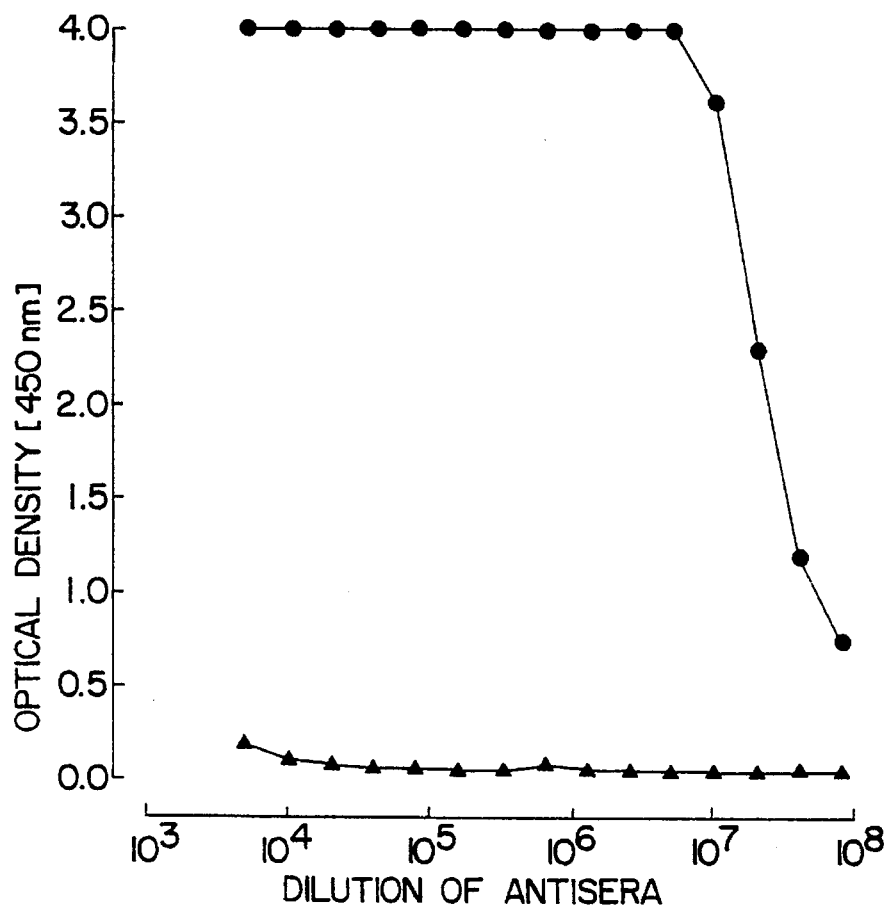
FIG. 6 is a graph illustrating the polyclonal anti-TP serum titers generated utilizing the immunization scheme described in Example 3 below. The circle represents the TP $(1–19)_8$-LC coated test plate and the solid triangle represents the control plate.

The results of this assay are illustrated in FIG. 6. This polyclonal antibody specific for HTP$_{(1-19)}$ bound to HTP$_{(1-19)}$ octameric MAP-coated plates with half-maximal binding occurring at 1:20,000,000 in PBS/Tween® 20 reagent, but showed minimal binding to ovalbumin-coated plates. This antibody was subsequently used in the ELISA for HTP described in the example below.

EXAMPLE 4

TP ELISA (Showing parallel curves with human plasma extract, Synthetic TP 1–52 and recombinant α-, β- and γTP)

To demonstrate the relationship between a synthetic TP AA 1–52 standard curve, recombinant TP, and serially diluted human plasma extracts, 8 ml human plasma were subjected to the dissociation and SepPak® cartridge extraction methods using a 20:80 ratio of 0.1% TFA: acetonitrile described in Example 2 above. The acetonitrile was removed from the extracted sample by evaporation in a heated block (40° C.) under a stream of nitrogen gas. The remaining aqueous phase was frozen and lyophilized to remove the TFA present. The dried sample was then resuspended in 1 ml TP assay buffer consisting of 0.05 M phosphate buffered physiologic saline containing 0.025 M ethylenediaminetetraacetic acid (EDTA), 0.04% sodium azide, 0.01% Tween® 20 reagent and 0.4% β-mercaptoethanol to obtain an 8×concentrated sample. The resuspended sample was then serially diluted with assay buffer and placed in the ELISA assay.

The samples were added at a volume of 200 μL/well to Immulon 4® polystyrene microtiter plates, that had been previously coated with rabbit anti-hTP 1–19 and post-coated with 1% BSA to prevent non-specific absorption. Synthetic hTP 1–52 was added to wells at concentration ranging from 100 to 1.56 pg/mL at a volume of 200 μL/well to serve as a standard curve. Serial dilutions of crude extracts of *E. coli* transfected to produce α-hTP, β-hTP and γ-hTP, and control *E. coli* extract, were also added to the wells. Buffer alone was added to wells to serve as O-binding controls (nonspecific binding). All sample, standard and reagent dilutions were made using 0.01 M phosphate buffered saline, pH 7.4 containing 0.5% bovine serum albumin and 0.05% Tween 20.

The samples/standards were incubated for 3 hrs at 37° C. The wells were then washed 3×with ELISA buffer and 200 μL biotinylated monoclonal antibody against hTP 29–50 [SEQ ID NO:2, 4, 6] added at an appropriate dilution in ELISA buffer containing 1% horse serum and incubated for 2 hours at 37° C. The wells were then washed 3×with ELISA buffer. Streptavidin, polyhorseradish peroxidase was added at a dilution of 1:5000 (200 μL volume) and the incubation continued at room temperature for 30 minutes. The wells were then washed 5×with ELISA buffer and Ultra-Blue® substrate added for an additional 30 minutes incubation at room temperature. The optical density of each well was determined as a direct index of the amount of TP present.

Figure 7A:
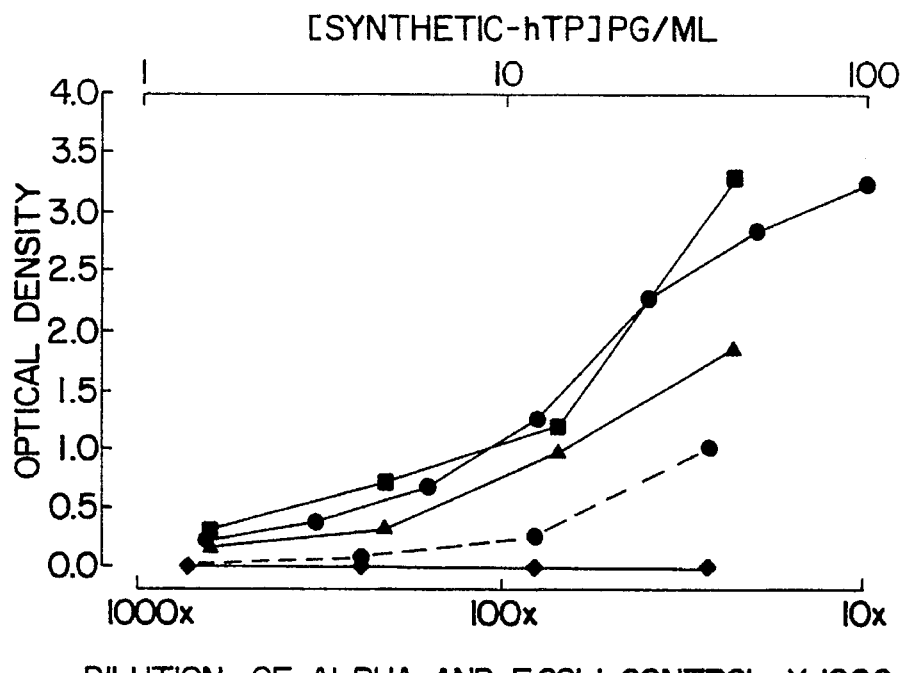
FIG. 7A is a line graph illustrating the parallel binding curves produced in the TP sandwich ELISA by serial dilutions of synthetic TP 1–52, human plasma extract and recombinant α, β and γ TP, as described in Example 4 below. In addition, the lack of binding produced by control *E. coli* (non-recombinant TP producing) extract is illustrated. The -●- represents synthetic hTP 1–52; --●-- represents αTP, ■ represents βTP, ▲ represents γTP and ♦ represents the *E. coli* control.
Figure 7B:
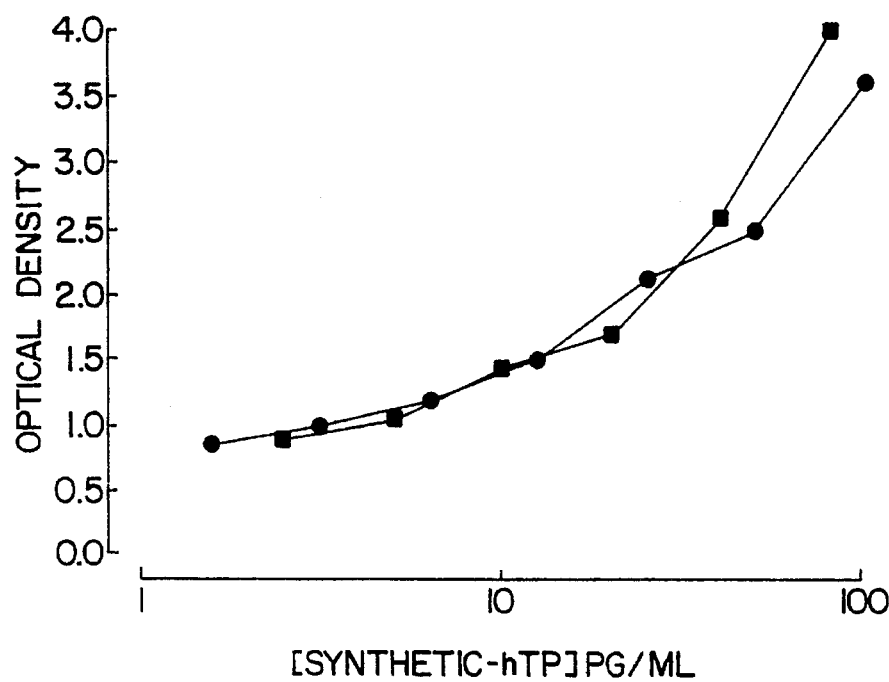
FIG. 7B is a binding curve produced by serial dilutions of synthetic TP 1–52 standard (●) and resuspended human plasma extracts (■).

FIGS. 7A and 7B illustrate the binding curves produced by serial dilutions of synthetic TP 1–52 standard, recombinant α-, β- and γ-TP standards (FIG. 7A) and resuspended human plasma extracts (FIG. 7B). Decreasing concentrations of the extracted human plasma produced a binding curve that was parallel to the binding curve produced by serial dilutions of the synthetic hTP 1–52 standard. Similarly, serial dilutions of the recombinant TP forms produced binding curves that were parallel to the binding curves produced by the synthetic hTP 1–52 standard. No hTP-like immunoreactivity was detected in the control *E. coli* extract. These results indicate the presence of similarly reactive epitopes in all of the hTP containing material tested and, therefore, the appropriateness of this application of the present invention to quantitate hTP immunoreactivity in human plasma.

EXAMPLE 5

Demonstration of Extraction Requirement to Separate TP from Interfering Plasma Substances Pooled plasma was prepared from blood collected from normal, healthy subjects. Eight mL of plasma were subjected to dissociation and extraction on a SepPak® cartridge as described in Example 2. The remainder of the sample pool was frozen until use. The dried extracted sample was resuspended in 1 mL TP assay buffer, serially diluted and subjected to the TP sandwich ELISA as described in Example 4. In addition, the previously frozen, unextracted plasma sample was placed in the assay both undiluted and serially diluted with buffer to a final dilution of 1:8.

Figure 8:
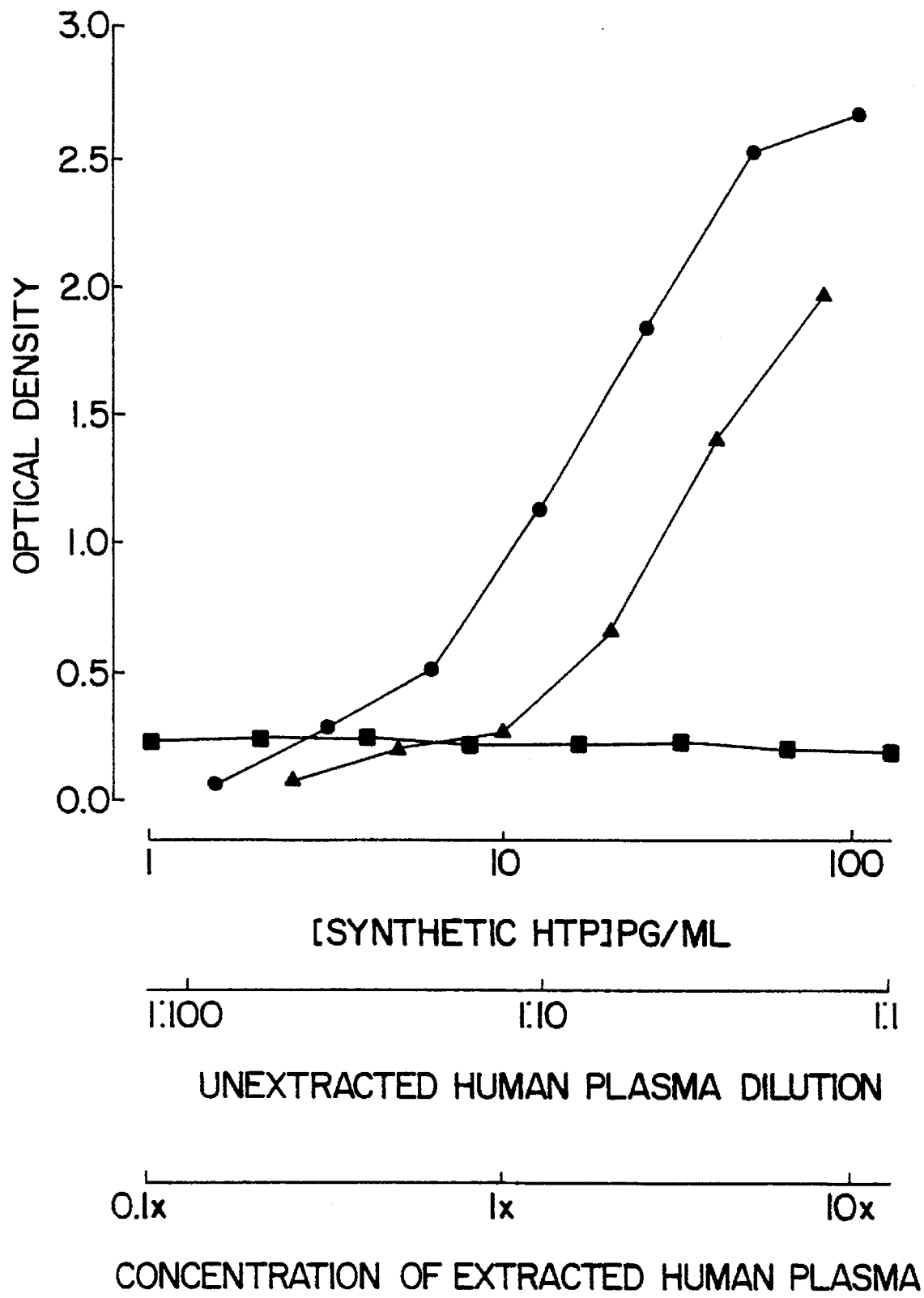
FIG. 8 is a graph illustrating the need for extraction prior to measuring TP in human plasma, as described in Example 5 below. Synthetic hTP 1–52 (●); extracted human plasma (▲); unextracted human plasma (■).

As illustrated in FIG. 8, addition of unextracted plasma to the assay plate failed to produce a positive reaction. Addition of extracted human plasma to the assay, however, produced a strong reading of TP-immunoreactivity in the assay that was both concentration dependent and parallel to the synthetic hTP 1–52 standard curve.

EXAMPLE 6

Demonstration of Age-Related Reduction in Human Plasma TP Levels as Measured by TP Sandwich ELISA Blood samples were withdrawn from 30 normal volunteers between 9 and 12 a.m. The blood was collected into EDTA-containing vacutainer tubes and placed on ice until processing. Following centrifugation at 1150×g to pellet the cells, the resultant plasma was transferred to polypropylene tubes and stored at −80° C. until assay.

To determine the level of plasma TP, 1.5 mL aliquots of plasma were extracted as described in Example 2 and subjected to TP sandwich ELISA as described in Example 4.

Figure 9:
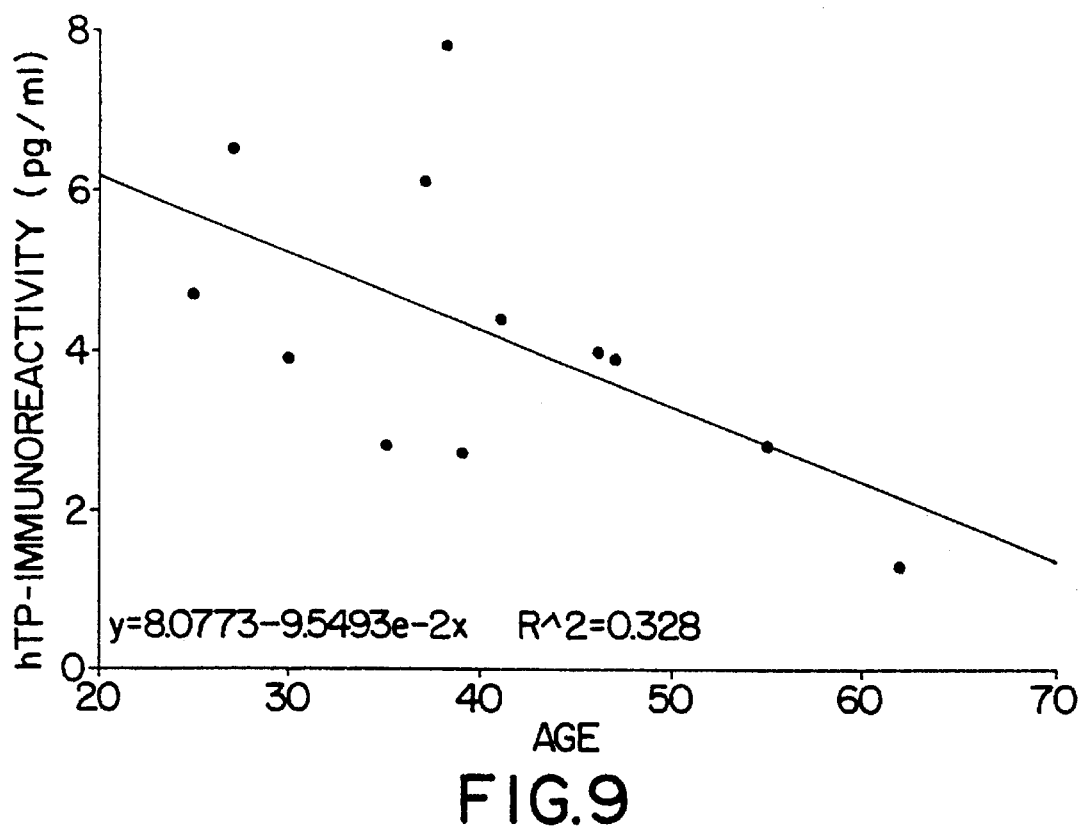
FIG. 9 is a graph illustrating the age-related reduction in plasma TP levels in female subjects, as measured by the method of the invention, as described in Example 6 below.
Figure 10:
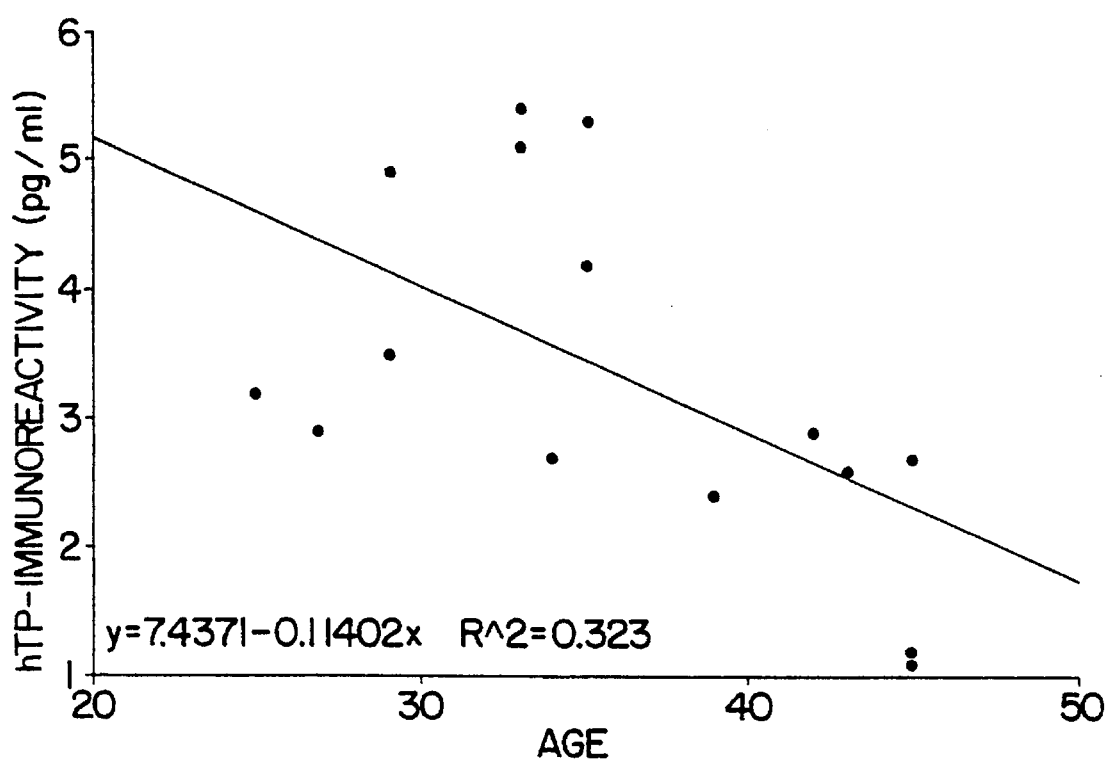
FIG. 10 is a graph illustrating the age-related reduction in plasma TP levels in male subjects, as measured by the method of the invention, as described in Example 6 below.

The results are illustrated in FIGS. 9 and 10. TP levels were higher in female subjects than in male subjects ($P<0.02$) and, in both sexes, were found to decline with age. For females, a significant linear relationship was observed between the age of subjects and plasma TP levels ($r^2=0.33$, P<0.05), with a mean decline of 0.10/ml/year. Similarly, for male subjects, a significant linear relationship was observed between the age of subjects and plasma TP levels ($r^2=0.32$, P<0.03), with a mean decline of 0.11 pg/ml/year. This decline in TP levels may be related to, and serve as an index of, the decline in immune function observed with increasing age.

Numerous modifications and variations of the present invention are included in the above-identified specification and are expected to be obvious to one of skill in the art. Such modifications and alterations to the processes of the present invention are believed to be encompassed in the scope of the claims appended hereto.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2490 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 205..2286

( x i ) SEQUENCE DESCRIPTION: SEQ ID NO:1:

```
GTTCGTAGTT  CGGCTCTGGG  GTCTTTTGTG  TCCGGGTCTG  GCTTGGCTTT  GTGTCCGCGA                                60

GTTTTTGTTC  CGCTCCGCAG  CGCTCTTCCC  GGGCAGGAGC  CGTGAGGCTC  GGAGGCGGCA                               120

GCGCGGTCCC  CGGCCAGGAG  CAAGCGCGCC  GGCGTGAGCG  GCGGCGGCAA  AGGCTGTGGG                               180

GAGGGGGCTT  CGCAGATCCC  CGAG ATG CCG GAG TTC CTG GAA GAC CCC TCG                                    231
                            Met Pro Glu Phe Leu Glu Asp Pro Ser
                             1               5

GTC CTG ACA AAA GAC AAG TTG AAG AGT GAG TTG GTC GCC AAC AAT GTG                                    279
Val Leu Thr Lys Asp Lys Leu Lys Ser Glu Leu Val Ala Asn Asn Val
 10              15                  20                  25

ACG CTG CCG GCC GGG GAG CAG CGC AAA GAC GTG TAC GTC CAG CTC TAC                                    327
Thr Leu Pro Ala Gly Glu Gln Arg Lys Asp Val Tyr Val Gln Leu Tyr
                 30                  35                  40

CTG CAG CAC CTC ACG GCT CGC AAC CGG CCG CCG CTC CCC GCC GGC ACC                                    375
Leu Gln His Leu Thr Ala Arg Asn Arg Pro Pro Leu Pro Ala Gly Thr
             45                  50                  55

AAC AGC AAG GGG CCC CCG GAC TTC TCC AGT GAC GAA GAG CGC GAG CCC                                    423
Asn Ser Lys Gly Pro Pro Asp Phe Ser Ser Asp Glu Glu Arg Glu Pro
         60                  65                  70

ACC CCG GTC CTC GGC TCT GGG GCC GCC GCC GCG GGC CGG AGC CGA GCA                                    471
Thr Pro Val Leu Gly Ser Gly Ala Ala Ala Ala Gly Arg Ser Arg Ala
     75                  80                  85

GCC GTC GGC AGG AAA GCC ACA AAA AAA ACT GAT AAA CCC AGA CAA GAA                                    519
Ala Val Gly Arg Lys Ala Thr Lys Lys Thr Asp Lys Pro Arg Gln Glu
 90                  95                 100                 105

GAT AAA GAT GAT CTA GAT GTA ACA GAG CTC ACT AAT GAA GAT CTT TTG                                    567
Asp Lys Asp Asp Leu Asp Val Thr Glu Leu Thr Asn Glu Asp Leu Leu
                110                 115                 120

GAT CAG CTT GTG AAA TAC GGA GTG AAT CCT GGT CCT ATT GTG GGA ACA                                    615
Asp Gln Leu Val Lys Tyr Gly Val Asn Pro Gly Pro Ile Val Gly Thr
            125                 130                 135

ACC AGG AAG CTA TAT GAG AAA AAG CTT TTG AAA CTG AGG GAA CAA GGA                                    663
Thr Arg Lys Leu Tyr Glu Lys Lys Leu Leu Lys Leu Arg Glu Gln Gly
        140                 145                 150

ACA GAA TCA AGA TCT TCT ACT CCT CTG CCA ACA ATT TCT TCT TCA GCA                                    711
```

```
Thr Glu Ser Arg Ser Ser Thr Pro Leu Pro Thr Ile Ser Ser Ser Ala
    155                 160                 165

GAA AAT ACA AGG CAG AAT GGA AGT AAT GAT TCT GAC AGA TAC AGT GAC      759
Glu Asn Thr Arg Gln Asn Gly Ser Asn Asp Ser Asp Arg Tyr Ser Asp
170                 175                 180                 185

AAT GAA GAA GGA AAG AAG AAA GAA CAC AAG AAA GTG AAG TCC ACT AGG      807
Asn Glu Glu Gly Lys Lys Lys Glu His Lys Lys Val Lys Ser Thr Arg
                190                 195                 200

GAT ATT GTT CCT TTT TCT GAA CTT GGA ACT ACT CCC TCT GGT GGT GGA      855
Asp Ile Val Pro Phe Ser Glu Leu Gly Thr Thr Pro Ser Gly Gly Gly
            205                 210                 215

TTT TTT CAG GGT ATT TCT TTT CCT GAA ATC TCC ACC CGT CCT CCT TTG      903
Phe Phe Gln Gly Ile Ser Phe Pro Glu Ile Ser Thr Arg Pro Pro Leu
        220                 225                 230

GGC AGT ACC GAA CTA CAG GCA GCT AAG AAA GTA CAT ACT TCT AAG GGA      951
Gly Ser Thr Glu Leu Gln Ala Ala Lys Lys Val His Thr Ser Lys Gly
    235                 240                 245

GAC CTA CCT AGG GAG CCT CTT GTT GCC ACA AAC TTG CCT GGC AGG GGA      999
Asp Leu Pro Arg Glu Pro Leu Val Ala Thr Asn Leu Pro Gly Arg Gly
250                 255                 260                 265

CAG TTG CAG AAG TTA GCC TCT GAA AGG AAT TTG TTT ATT TCA TGC AAG     1047
Gln Leu Gln Lys Leu Ala Ser Glu Arg Asn Leu Phe Ile Ser Cys Lys
                270                 275                 280

TCT AGC CAT GAT AGG TGT TTA GAG AAA AGT TCT TCG TCA TCT TCT CAG     1095
Ser Ser His Asp Arg Cys Leu Glu Lys Ser Ser Ser Ser Ser Ser Gln
            285                 290                 295

CCT GAA CAC AGT GCC ATG TTG GTC TCT ACT GCA GCT TCT CCT TCA CTG     1143
Pro Glu His Ser Ala Met Leu Val Ser Thr Ala Ala Ser Pro Ser Leu
        300                 305                 310

ATT AAA GAA ACC ACC ACT GGT TAC TAT AAA GAC ATA GTA GAA AAT ATT     1191
Ile Lys Glu Thr Thr Thr Gly Tyr Tyr Lys Asp Ile Val Glu Asn Ile
    315                 320                 325

TGC GGT AGA GAG AAA AGT GGA ATT CAA CCA TTA TGT CCT GAG AGG TCC     1239
Cys Gly Arg Glu Lys Ser Gly Ile Gln Pro Leu Cys Pro Glu Arg Ser
330                 335                 340                 345

CAT ATT TCA GAT CAA TCG CCT CTC TCC AGT AAA AGG AAA GCA CTA GAA     1287
His Ile Ser Asp Gln Ser Pro Leu Ser Ser Lys Arg Lys Ala Leu Glu
                350                 355                 360

GAG TCT GAG AGC TCA CAA CTA ATT TCT CCG CCA CTT GCC CAG GCA ATC     1335
Glu Ser Glu Ser Ser Gln Leu Ile Ser Pro Pro Leu Ala Gln Ala Ile
            365                 370                 375

AGA GAT TAT GTC AAT TCT CTG TTG GTC CAG GGT GGG GTA GGT AGT TTG     1383
Arg Asp Tyr Val Asn Ser Leu Leu Val Gln Gly Gly Val Gly Ser Leu
        380                 385                 390

CCT GGA ACT TCT AAC TCT ATG CCC CCA CTG GAT GTA GAA AAC ATA CAG     1431
Pro Gly Thr Ser Asn Ser Met Pro Pro Leu Asp Val Glu Asn Ile Gln
    395                 400                 405

AAG AGA ATT GAT CAG TCT AAG TTT CAA GAA ACT GAA TTC CTG TCT CCT     1479
Lys Arg Ile Asp Gln Ser Lys Phe Gln Glu Thr Glu Phe Leu Ser Pro
410                 415                 420                 425

CCA AGA AAA GTC CCT AGA CTG AGT GAG AAG TCA GTG GAG GAA AGG GAT     1527
Pro Arg Lys Val Pro Arg Leu Ser Glu Lys Ser Val Glu Glu Arg Asp
                430                 435                 440

TCA GGT TCC TTT GTG GCA TTT CAG AAC ATA CCT GGA TCC GAA CTG ATG     1575
Ser Gly Ser Phe Val Ala Phe Gln Asn Ile Pro Gly Ser Glu Leu Met
            445                 450                 455

TCT TCT TTT GCC AAA ACT GTT GTC TCT CAT TCA CTC ACT ACC TTA GGT     1623
Ser Ser Phe Ala Lys Thr Val Val Ser His Ser Leu Thr Thr Leu Gly
        460                 465                 470

CTA GAA GTG GCT AAG CAA TCA CAG CAT GAT AAA ATA GAT GCC TCA GAA     1671
```

```
         Leu Glu Val Ala Lys Gln Ser Gln His Asp Lys Ile Asp Ala Ser Glu
             475                 480                 485

CTA TCT TTT CCC TTC CAT GAA TCT ATT TTA AAA GTA ATT GAA GAA GAA         1719
Leu Ser Phe Pro Phe His Glu Ser Ile Leu Lys Val Ile Glu Glu Glu
490                 495                 500                 505

TGG CAG CAA GTT GAC AGG CAG CTG CCT TCA CTG GCA TGC AAA TAT CCA         1767
Trp Gln Gln Val Asp Arg Gln Leu Pro Ser Leu Ala Cys Lys Tyr Pro
                510                 515                 520

GTT TCT TCC AGG GAG GCA ACA CAG ATA TTA TCA GTT CCA AAA GTA GAT         1815
Val Ser Ser Arg Glu Ala Thr Gln Ile Leu Ser Val Pro Lys Val Asp
            525                 530                 535

GAT GAA ATC CTA GGG TTT ATT TCT GAA GCC ACT CCA CTA GGA GGT ATT         1863
Asp Glu Ile Leu Gly Phe Ile Ser Glu Ala Thr Pro Leu Gly Gly Ile
        540                 545                 550

CAA GCA GCC TCC ACT GAG TCT TGC AAT CAG CAG TTG GAC TTA GCA CTC         1911
Gln Ala Ala Ser Thr Glu Ser Cys Asn Gln Gln Leu Asp Leu Ala Leu
    555                 560                 565

TGT AGA GCA TAT GAA GCT GCA GCA TCA GCA TTG CAG ATT GCA ACT CAC         1959
Cys Arg Ala Tyr Glu Ala Ala Ala Ser Ala Leu Gln Ile Ala Thr His
570                 575                 580                 585

ACT GCC TTT GTA GCT AAG GCT ATG CAG GCA GAC ATT AGT CAA GCT GCA         2007
Thr Ala Phe Val Ala Lys Ala Met Gln Ala Asp Ile Ser Gln Ala Ala
                590                 595                 600

CAG ATT CTT AGC TCA GAT CCT AGT CGT ACC CAC CAA GCG CTT GGG ATT         2055
Gln Ile Leu Ser Ser Asp Pro Ser Arg Thr His Gln Ala Leu Gly Ile
            605                 610                 615

CTG AGC AAA ACA TAT GAT GCA GCC TCA TAT ATT TGT GAA GCT GCA TTT         2103
Leu Ser Lys Thr Tyr Asp Ala Ala Ser Tyr Ile Cys Glu Ala Ala Phe
        620                 625                 630

GAT GAA GTG AAG ATG GCT GCC CAT ACC ATG GGA AAT GCC ACT GTA GGT         2151
Asp Glu Val Lys Met Ala Ala His Thr Met Gly Asn Ala Thr Val Gly
    635                 640                 645

CGT CGA TAC CTC TGG CTG AAG GAT TGC AAA ATT AAT TTA GCT TCT AAG         2199
Arg Arg Tyr Leu Trp Leu Lys Asp Cys Lys Ile Asn Leu Ala Ser Lys
650                 655                 660                 665

AAT AAG CTG GCT TCC ACT CCC TTT AAA GGT GGA ACA TTA TTT GGA GGA         2247
Asn Lys Leu Ala Ser Thr Pro Phe Lys Gly Gly Thr Leu Phe Gly Gly
                670                 675                 680

GAA GTA TGC AAA GTA ATT AAA AAG CGT GGA AAT AAA CAC TAGTAAAATT         2296
Glu Val Cys Lys Val Ile Lys Lys Arg Gly Asn Lys His
            685                 690

AAGGACAAAA AGACATCTAT CTTATCTTTC AGGTACTTTA TGCCAACATT TTCTTTTCTG      2356

TTAAGGTTGT TTTAGTTTCC AGATAGGGCT AATTACAAAA TGTTAAGCTT CTACCCATCA      2416

AATTACAGTA TAAAAGTAAT TGCCTGTGTA GAACTACTTG TCTTTTCTAA AGATTTGCGT      2476

AGATAGGAAG CCTG                                                        2490
```

( 2 ) INFORMATION FOR SEQ ID NO:2:

( i ) SEQUENCE CHARACTERISTICS:
        ( A ) LENGTH: 694 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Glu Phe Leu Glu Asp Pro Ser Val Leu Thr Lys Asp Lys Leu
 1               5                  10                  15

Lys Ser Glu Leu Val Ala Asn Asn Val Thr Leu Pro Ala Gly Glu Gln
                20                  25                  30
```

```
Arg Lys Asp Val Tyr Val Gln Leu Tyr Leu Gln His Leu Thr Ala Arg
        35              40                  45

Asn Arg Pro Pro Leu Pro Ala Gly Thr Asn Ser Lys Gly Pro Pro Asp
    50              55                  60

Phe Ser Ser Asp Glu Glu Arg Glu Pro Thr Pro Val Leu Gly Ser Gly
65              70                  75                      80

Ala Ala Ala Ala Gly Arg Ser Arg Ala Ala Val Gly Arg Lys Ala Thr
                85                  90                  95

Lys Lys Thr Asp Lys Pro Arg Gln Glu Asp Lys Asp Asp Leu Asp Val
            100             105             110

Thr Glu Leu Thr Asn Glu Asp Leu Leu Asp Gln Leu Val Lys Tyr Gly
            115             120             125

Val Asn Pro Gly Pro Ile Val Gly Thr Thr Arg Lys Leu Tyr Glu Lys
    130             135             140

Lys Leu Leu Lys Leu Arg Glu Gln Gly Thr Glu Ser Arg Ser Ser Thr
145             150             155                         160

Pro Leu Pro Thr Ile Ser Ser Ser Ala Glu Asn Thr Arg Gln Asn Gly
            165             170             175

Ser Asn Asp Ser Asp Arg Tyr Ser Asp Asn Glu Glu Gly Lys Lys Lys
            180             185             190

Glu His Lys Lys Val Lys Ser Thr Arg Asp Ile Val Pro Phe Ser Glu
        195             200             205

Leu Gly Thr Thr Pro Ser Gly Gly Phe Phe Gln Gly Ile Ser Phe
    210             215             220

Pro Glu Ile Ser Thr Arg Pro Pro Leu Gly Ser Thr Glu Leu Gln Ala
225             230             235                         240

Ala Lys Lys Val His Thr Ser Lys Gly Asp Leu Pro Arg Glu Pro Leu
            245             250             255

Val Ala Thr Asn Leu Pro Gly Arg Gly Gln Leu Gln Lys Leu Ala Ser
            260             265             270

Glu Arg Asn Leu Phe Ile Ser Cys Lys Ser Ser His Asp Arg Cys Leu
        275             280             285

Glu Lys Ser Ser Ser Ser Ser Gln Pro Glu His Ser Ala Met Leu
    290             295             300

Val Ser Thr Ala Ala Ser Pro Ser Leu Ile Lys Glu Thr Thr Thr Gly
305             310             315                         320

Tyr Tyr Lys Asp Ile Val Glu Asn Ile Cys Gly Arg Glu Lys Ser Gly
            325             330             335

Ile Gln Pro Leu Cys Pro Glu Arg Ser His Ile Ser Asp Gln Ser Pro
            340             345             350

Leu Ser Ser Lys Arg Lys Ala Leu Glu Glu Ser Glu Ser Ser Gln Leu
            355             360             365

Ile Ser Pro Pro Leu Ala Ala Ile Arg Asp Tyr Val Asn Ser Leu
    370             375             380

Leu Val Gln Gly Gly Val Gly Ser Leu Pro Gly Thr Ser Asn Ser Met
385             390             395                         400

Pro Pro Leu Asp Val Glu Asn Ile Gln Lys Arg Ile Asp Gln Ser Lys
            405             410             415

Phe Gln Glu Thr Glu Phe Leu Ser Pro Pro Arg Lys Val Pro Arg Leu
            420             425             430

Ser Glu Lys Ser Val Glu Glu Arg Asp Ser Gly Ser Phe Val Ala Phe
        435             440             445

Gln Asn Ile Pro Gly Ser Glu Leu Met Ser Ser Phe Ala Lys Thr Val
```

```
                450                      455                      460
Val  Ser  His  Ser  Leu  Thr  Thr  Leu  Gly  Leu  Glu  Val  Ala  Lys  Gln  Ser
465                      470                      475                      480

Gln  His  Asp  Lys  Ile  Asp  Ala  Ser  Glu  Leu  Ser  Phe  Pro  Phe  His  Glu
                    485                      490                      495

Ser  Ile  Leu  Lys  Val  Ile  Glu  Glu  Glu  Trp  Gln  Gln  Val  Asp  Arg  Gln
                    500                      505                      510

Leu  Pro  Ser  Leu  Ala  Cys  Lys  Tyr  Pro  Val  Ser  Ser  Arg  Glu  Ala  Thr
               515                      520                      525

Gln  Ile  Leu  Ser  Val  Pro  Lys  Val  Asp  Asp  Glu  Ile  Leu  Gly  Phe  Ile
               530                      535                      540

Ser  Glu  Ala  Thr  Pro  Leu  Gly  Gly  Ile  Gln  Ala  Ala  Ser  Thr  Glu  Ser
545                      550                      555                      560

Cys  Asn  Gln  Gln  Leu  Asp  Leu  Ala  Leu  Cys  Arg  Ala  Tyr  Glu  Ala  Ala
                    565                      570                      575

Ala  Ser  Ala  Leu  Gln  Ile  Ala  Thr  His  Thr  Ala  Phe  Val  Ala  Lys  Ala
               580                      585                      590

Met  Gln  Ala  Asp  Ile  Ser  Gln  Ala  Ala  Gln  Ile  Leu  Ser  Ser  Asp  Pro
          595                      600                      605

Ser  Arg  Thr  His  Gln  Ala  Leu  Gly  Ile  Leu  Ser  Lys  Thr  Tyr  Asp  Ala
     610                      615                      620

Ala  Ser  Tyr  Ile  Cys  Glu  Ala  Ala  Phe  Asp  Glu  Val  Lys  Met  Ala  Ala
625                      630                      635                      640

His  Thr  Met  Gly  Asn  Ala  Thr  Val  Gly  Arg  Arg  Tyr  Leu  Trp  Leu  Lys
                    645                      650                      655

Asp  Cys  Lys  Ile  Asn  Leu  Ala  Ser  Lys  Asn  Lys  Leu  Ala  Ser  Thr  Pro
                660                      665                      670

Phe  Lys  Gly  Gly  Thr  Leu  Phe  Gly  Gly  Glu  Val  Cys  Lys  Val  Ile  Lys
               675                      680                      685

Lys  Arg  Gly  Asn  Lys  His
     690
```

( 2 ) INFORMATION FOR SEQ ID NO:3:

( i ) SEQUENCE CHARACTERISTICS:
        ( A ) LENGTH: 1743 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 238..1599

( x i ) SEQUENCE DESCRIPTION: SEQ ID NO:3:

```
GGTTGGTGCG  AGCTTCCAGC  TTGGCCGCAG  TTGGTTCGTA  GTTCGGCTCT  GGGGTCTTTT      60

GTGTCCGGGT  CTGGCTTGGC  TTTGTGTCCG  CGAGTTTTTG  TTCCGCTCCG  CAGCGCTCTT     120

CCCGGGCAGG  AGCCGTGAGG  CTCGGAGGCG  GCAGCGCGGT  CCCCGGCCAG  GAGCAAGCGC     180

GCCGGCGTGA  GCGGCGGCGG  CAAAGGCTGT  GGGGAGGGGG  CTTCGCAGAT  CCCCGAG        237

ATG  CCG  GAG  TTC  CTG  GAA  GAC  CCC  TCG  GTC  CTG  ACA  AAA  GAC  AAG  TTG    285
Met  Pro  Glu  Phe  Leu  Glu  Asp  Pro  Ser  Val  Leu  Thr  Lys  Asp  Lys  Leu
 1                 5                      10                      15

AAG  AGT  GAG  TTG  GTC  GCC  AAC  AAT  GTG  ACG  CTG  CCG  GCC  GGG  GAG  CAG    333
Lys  Ser  Glu  Leu  Val  Ala  Asn  Asn  Val  Thr  Leu  Pro  Ala  Gly  Glu  Gln
            20                      25                      30
```

| | | | | | | | | | | | | | | | | |
|---|---|---|---|---|---|---|---|---|---|---|---|---|---|---|---|---|
| CGC | AAA | GAC | GTG | TAC | GTC | CAG | CTC | TAC | CTG | CAG | CAC | CTC | ACG | GCT | CGC | 381 |
| Arg | Lys | Asp | Val | Tyr | Val | Gln | Leu | Tyr | Leu | Gln | His | Leu | Thr | Ala | Arg | |
| | | 35 | | | | 40 | | | | | | 45 | | | | |
| AAC | CGG | CCG | CCG | CTC | CCC | GCC | GGC | ACC | AAC | AGC | AAG | GGG | CCC | CCG | GAC | 429 |
| Asn | Arg | Pro | Pro | Leu | Pro | Ala | Gly | Thr | Asn | Ser | Lys | Gly | Pro | Pro | Asp | |
| | 50 | | | | | 55 | | | | | 60 | | | | | |
| TTC | TCC | AGT | GAC | GAA | GAG | CGC | GAG | CCC | ACC | CCG | GTC | CTC | GGC | TCT | GGG | 477 |
| Phe | Ser | Ser | Asp | Glu | Glu | Arg | Glu | Pro | Thr | Pro | Val | Leu | Gly | Ser | Gly | |
| 65 | | | | | 70 | | | | | 75 | | | | | 80 | |
| GCC | GCC | GCC | GCG | GGC | CGG | AGC | CGA | GCA | GCC | GTC | GGC | AGG | AAA | GCC | ACA | 525 |
| Ala | Ala | Ala | Ala | Gly | Arg | Ser | Arg | Ala | Ala | Val | Gly | Arg | Lys | Ala | Thr | |
| | | | | 85 | | | | | 90 | | | | | 95 | | |
| AAA | AAA | ACT | GAT | AAA | CCC | AGA | CAA | GAA | GAT | AAA | GAT | GAT | CTA | GAT | GTA | 573 |
| Lys | Lys | Thr | Asp | Lys | Pro | Arg | Gln | Glu | Asp | Lys | Asp | Asp | Leu | Asp | Val | |
| | | | 100 | | | | | 105 | | | | | 110 | | | |
| ACA | GAG | CTC | ACT | AAT | GAA | GAT | CTT | TTG | GAT | CAG | CTT | GTG | AAA | TAC | GGA | 621 |
| Thr | Glu | Leu | Thr | Asn | Glu | Asp | Leu | Leu | Asp | Gln | Leu | Val | Lys | Tyr | Gly | |
| | | | 115 | | | | | 120 | | | | | 125 | | | |
| GTG | AAT | CCT | GGT | CCT | ATT | GTG | GGA | ACA | ACC | AGG | AAG | CTA | TAT | GAG | AAA | 669 |
| Val | Asn | Pro | Gly | Pro | Ile | Val | Gly | Thr | Thr | Arg | Lys | Leu | Tyr | Glu | Lys | |
| | 130 | | | | | 135 | | | | | 140 | | | | | |
| AAG | CTT | TTG | AAA | CTG | AGG | GAA | CAA | GGA | ACA | GAA | TCA | AGA | TCT | TCT | ACT | 717 |
| Lys | Leu | Leu | Lys | Leu | Arg | Glu | Gln | Gly | Thr | Glu | Ser | Arg | Ser | Ser | Thr | |
| 145 | | | | | 150 | | | | | 155 | | | | | 160 | |
| CCT | CTG | CCA | ACA | ATT | TCT | TCT | TCA | GCA | GAA | AAT | ACA | AGG | CAG | AAT | GGA | 765 |
| Pro | Leu | Pro | Thr | Ile | Ser | Ser | Ser | Ala | Glu | Asn | Thr | Arg | Gln | Asn | Gly | |
| | | | | 165 | | | | | 170 | | | | | 175 | | |
| AGT | AAT | GAT | TCT | GAC | AGA | TAC | AGT | GAC | AAT | GAA | GAA | GAC | TCT | AAA | ATA | 813 |
| Ser | Asn | Asp | Ser | Asp | Arg | Tyr | Ser | Asp | Asn | Glu | Glu | Asp | Ser | Lys | Ile | |
| | | | 180 | | | | | 185 | | | | | 190 | | | |
| GAG | CTC | AAG | CTT | GAG | AAG | AGA | GAA | CCA | CTA | AAG | GGC | AGA | GCA | AAG | ACT | 861 |
| Glu | Leu | Lys | Leu | Glu | Lys | Arg | Glu | Pro | Leu | Lys | Gly | Arg | Ala | Lys | Thr | |
| | | 195 | | | | | 200 | | | | | 205 | | | | |
| CCA | GTA | ACA | CTC | AAG | CAA | AGA | AGA | GTT | GAG | CAC | AAT | CAG | AGC | TAT | TCT | 909 |
| Pro | Val | Thr | Leu | Lys | Gln | Arg | Arg | Val | Glu | His | Asn | Gln | Ser | Tyr | Ser | |
| | 210 | | | | | 215 | | | | | 220 | | | | | |
| CAA | GCT | GGA | ATA | ACT | GAG | ACT | GAA | TGG | ACA | AGT | GGA | TCT | TCA | AAA | GGC | 957 |
| Gln | Ala | Gly | Ile | Thr | Glu | Thr | Glu | Trp | Thr | Ser | Gly | Ser | Ser | Lys | Gly | |
| 225 | | | | | 230 | | | | | 235 | | | | | 240 | |
| GGA | CCT | CTG | CAG | GCA | TTA | ACT | AGG | GAA | TCT | ACA | AGA | GGG | TCA | AGA | AGA | 1005 |
| Gly | Pro | Leu | Gln | Ala | Leu | Thr | Arg | Glu | Ser | Thr | Arg | Gly | Ser | Arg | Arg | |
| | | | | 245 | | | | | 250 | | | | | 255 | | |
| ACT | CCA | AGG | AAA | AGG | GTG | GAA | ACT | TCA | GAA | CAT | TTT | CGT | ATA | GAT | GGT | 1053 |
| Thr | Pro | Arg | Lys | Arg | Val | Glu | Thr | Ser | Glu | His | Phe | Arg | Ile | Asp | Gly | |
| | | | 260 | | | | | 265 | | | | | 270 | | | |
| CCA | GTA | ATT | TCA | GAG | AGT | ACT | CCC | ATA | GCT | GAA | ACT | ATA | ATG | GCT | TCA | 1101 |
| Pro | Val | Ile | Ser | Glu | Ser | Thr | Pro | Ile | Ala | Glu | Thr | Ile | Met | Ala | Ser | |
| | | 275 | | | | | 280 | | | | | 285 | | | | |
| AGC | AAC | GAA | TCC | TTA | GTT | GTC | AAT | AGG | GTG | ACT | GGA | AAT | TTC | AAG | CAT | 1149 |
| Ser | Asn | Glu | Ser | Leu | Val | Val | Asn | Arg | Val | Thr | Gly | Asn | Phe | Lys | His | |
| | 290 | | | | | 295 | | | | | 300 | | | | | |
| GCA | TCT | CCT | ATT | CTG | CCA | ATC | ACT | GAA | TTC | TCA | GAC | ATA | CCC | AGA | AGA | 1197 |
| Ala | Ser | Pro | Ile | Leu | Pro | Ile | Thr | Glu | Phe | Ser | Asp | Ile | Pro | Arg | Arg | |
| 305 | | | | | 310 | | | | | 315 | | | | | 320 | |
| GCA | CCA | AAG | AAA | CCA | TTG | ACA | AGA | GCT | GAA | GTG | GGA | GAA | AAA | ACA | GAG | 1245 |
| Ala | Pro | Lys | Lys | Pro | Leu | Thr | Arg | Ala | Glu | Val | Gly | Glu | Lys | Thr | Glu | |
| | | | | 325 | | | | | 330 | | | | | 335 | | |
| GAA | AGA | AGA | GTA | GAA | AGG | GAT | ATT | CTT | AAG | GAA | ATG | TTC | CCC | TAT | GAA | 1293 |
| Glu | Arg | Arg | Val | Glu | Arg | Asp | Ile | Leu | Lys | Glu | Met | Phe | Pro | Tyr | Glu | |
| | | | 340 | | | | | 345 | | | | | 350 | | | |

| | | | | | | | | | | | | | | | | |
|---|---|---|---|---|---|---|---|---|---|---|---|---|---|---|---|---|
| GCA | TCT | ACA | CCA | ACA | GGA | ATT | AGT | GCT | AGT | TGC | CGC | AGA | CCA | ATC | AAA | 1341 |
| Ala | Ser | Thr | Pro | Thr | Gly | Ile | Ser | Ala | Ser | Cys | Arg | Arg | Pro | Ile | Lys | |
| | | 355 | | | | 360 | | | | | 365 | | | | | |
| GGG | GCT | GCA | GGC | CGG | CCA | TTA | GAA | CTC | AGT | GAT | TTC | AGG | ATG | GAG | GAG | 1389 |
| Gly | Ala | Ala | Gly | Arg | Pro | Leu | Glu | Leu | Ser | Asp | Phe | Arg | Met | Glu | Glu | |
| 370 | | | | | 375 | | | | | 380 | | | | | | |
| TCT | TTT | TCA | TCT | AAA | TAT | GTT | CCT | AAG | TAT | GTT | CCC | TTG | GCA | GAT | GTC | 1437 |
| Ser | Phe | Ser | Ser | Lys | Tyr | Val | Pro | Lys | Tyr | Val | Pro | Leu | Ala | Asp | Val | |
| 385 | | | | | 390 | | | | | 395 | | | | | 400 | |
| AAG | TCA | GAA | AAG | ACA | AAA | AAG | GGA | CGC | TCC | ATT | CCC | GTA | TGG | ATA | AAA | 1485 |
| Lys | Ser | Glu | Lys | Thr | Lys | Lys | Gly | Arg | Ser | Ile | Pro | Val | Trp | Ile | Lys | |
| | | | | 405 | | | | | 410 | | | | | 415 | | |
| ATT | TTG | CTG | TTT | GTT | GTT | GTG | GCA | GTT | TTT | TTG | TTT | TTG | GTC | TAT | CAA | 1533 |
| Ile | Leu | Leu | Phe | Val | Val | Val | Ala | Val | Phe | Leu | Phe | Leu | Val | Tyr | Gln | |
| | | | 420 | | | | | 425 | | | | | 430 | | | |
| GCT | ATG | GAA | ACC | AAC | CAA | GTA | AAT | CCC | TTC | TCT | AAT | TTT | CTT | CAT | GTT | 1581 |
| Ala | Met | Glu | Thr | Asn | Gln | Val | Asn | Pro | Phe | Ser | Asn | Phe | Leu | His | Val | |
| | | 435 | | | | | 440 | | | | | 445 | | | | |
| GAC | CCT | AGA | AAA | TCC | AAC | TGAATGGTAT | | CTCTTTGGCA | | CGTTCAACTT | | | | | | 1629 |
| Asp | Pro | Arg | Lys | Ser | Asn | | | | | | | | | | | |
| | 450 | | | | | | | | | | | | | | | |

GGTCTCCTAT TTTCAATAAC TGTTGAAAAA CATTTGTGTA CACTTGTTGA CTCCAAGAAC  1689

TAAAAATAAT GTGATTTCGC CTCAATAAAT GTAGTATTTC ATTGAAAAGC AAAC  1743

( 2 ) INFORMATION FOR SEQ ID NO:4:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Pro | Glu | Phe | Leu | Glu | Asp | Pro | Ser | Val | Leu | Thr | Lys | Asp | Lys | Leu |
| 1 | | | | 5 | | | | | 10 | | | | | 15 | |
| Lys | Ser | Glu | Leu | Val | Ala | Asn | Asn | Val | Thr | Leu | Pro | Ala | Gly | Glu | Gln |
| | | | 20 | | | | | 25 | | | | | 30 | | |
| Arg | Lys | Asp | Val | Tyr | Val | Gln | Leu | Tyr | Leu | Gln | His | Leu | Thr | Ala | Arg |
| | | | 35 | | | | 40 | | | | | 45 | | | |
| Asn | Arg | Pro | Pro | Leu | Pro | Ala | Gly | Thr | Asn | Ser | Lys | Gly | Pro | Pro | Asp |
| | 50 | | | | | 55 | | | | | 60 | | | | |
| Phe | Ser | Ser | Asp | Glu | Glu | Arg | Glu | Pro | Thr | Pro | Val | Leu | Gly | Ser | Gly |
| 65 | | | | | 70 | | | | | 75 | | | | | 80 |
| Ala | Ala | Ala | Ala | Gly | Arg | Ser | Arg | Ala | Ala | Val | Gly | Arg | Lys | Ala | Thr |
| | | | | 85 | | | | | 90 | | | | | 95 | |
| Lys | Lys | Thr | Asp | Lys | Pro | Arg | Gln | Glu | Asp | Lys | Asp | Leu | Asp | Val | |
| | | | 100 | | | | | 105 | | | | | 110 | | |
| Thr | Glu | Leu | Thr | Asn | Glu | Asp | Leu | Leu | Asp | Gln | Leu | Val | Lys | Tyr | Gly |
| | | | 115 | | | | 120 | | | | | 125 | | | |
| Val | Asn | Pro | Gly | Pro | Ile | Val | Gly | Thr | Thr | Arg | Lys | Leu | Tyr | Glu | Lys |
| | | 130 | | | | 135 | | | | | 140 | | | | |
| Lys | Leu | Leu | Lys | Leu | Arg | Glu | Gln | Gly | Thr | Glu | Ser | Arg | Ser | Ser | Thr |
| 145 | | | | 150 | | | | | 155 | | | | | | 160 |
| Pro | Leu | Pro | Thr | Ile | Ser | Ser | Ser | Ala | Glu | Asn | Thr | Arg | Gln | Asn | Gly |
| | | | | 165 | | | | | 170 | | | | | 175 | |
| Ser | Asn | Asp | Ser | Asp | Arg | Tyr | Ser | Asp | Asn | Glu | Glu | Asp | Ser | Lys | Ile |
| | | | 180 | | | | | 185 | | | | | 190 | | |

| | | | | | | | | | | | | |
|---|---|---|---|---|---|---|---|---|---|---|---|---|
| Glu | Leu | Lys<br>195 | Leu | Glu | Lys | Arg<br>200 | Glu | Pro | Leu | Lys<br>205 | Gly | Arg | Ala | Lys | Thr |
| Pro | Val | Thr<br>210 | Leu | Lys | Gln | Arg<br>215 | Arg | Val | Glu | His<br>220 | Asn | Gln | Ser | Tyr | Ser |
| Gln<br>225 | Ala | Gly | Ile | Thr<br>230 | Glu | Thr | Glu | Trp | Thr<br>235 | Ser | Gly | Ser | Ser | Lys | Gly<br>240 |
| Gly | Pro | Leu | Gln | Ala<br>245 | Leu | Thr | Arg | Glu | Ser<br>250 | Thr | Arg | Gly | Ser<br>255 | Arg | Arg |
| Thr | Pro | Arg | Lys<br>260 | Arg | Val | Glu | Thr | Ser<br>265 | Glu | His | Phe | Arg | Ile<br>270 | Asp | Gly |
| Pro | Val | Ile<br>275 | Ser | Glu | Ser | Thr | Pro<br>280 | Ile | Ala | Glu | Thr | Ile<br>285 | Met | Ala | Ser |
| Ser | Asn<br>290 | Glu | Ser | Leu | Val<br>295 | Val | Asn | Arg | Val | Thr<br>300 | Gly | Asn | Phe | Lys | His |
| Ala<br>305 | Ser | Pro | Ile | Leu | Pro<br>310 | Ile | Thr | Glu | Phe | Ser<br>315 | Asp | Ile | Pro | Arg | Arg<br>320 |
| Ala | Pro | Lys | Lys | Pro<br>325 | Leu | Thr | Arg | Ala | Glu<br>330 | Val | Gly | Glu | Lys | Thr<br>335 | Glu |
| Glu | Arg | Arg | Val<br>340 | Glu | Arg | Asp | Ile | Leu<br>345 | Lys | Glu | Met | Phe | Pro<br>350 | Tyr | Glu |
| Ala | Ser | Thr<br>355 | Pro | Thr | Gly | Ile | Ser<br>360 | Ala | Ser | Cys | Arg | Arg<br>365 | Pro | Ile | Lys |
| Gly | Ala<br>370 | Ala | Gly | Arg | Pro | Leu<br>375 | Glu | Leu | Ser | Asp | Phe<br>380 | Arg | Met | Glu | Glu |
| Ser<br>385 | Phe | Ser | Ser | Lys | Tyr<br>390 | Val | Pro | Lys | Tyr<br>395 | Val | Pro | Leu | Ala | Asp | Val<br>400 |
| Lys | Ser | Glu | Lys | Thr<br>405 | Lys | Lys | Gly | Arg | Ser<br>410 | Ile | Pro | Val | Trp | Ile<br>415 | Lys |
| Ile | Leu | Leu | Phe<br>420 | Val | Val | Val | Ala | Val<br>425 | Phe | Leu | Phe | Leu | Val<br>430 | Tyr | Gln |
| Ala | Met | Glu<br>435 | Thr | Asn | Gln | Val | Asn<br>440 | Pro | Phe | Ser | Asn | Phe<br>445 | Leu | His | Val |
| Asp | Pro | Arg | Lys | Ser | Asn<br>450 | | | | | | | | | | |

( 2 ) INFORMATION FOR SEQ ID NO:5:

( i ) SEQUENCE CHARACTERISTICS:
        ( A ) LENGTH: 2392 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 241..1275

( x i ) SEQUENCE DESCRIPTION: SEQ ID NO:5:

| | | | | | |
|---|---|---|---|---|---|
| CCCTGCTACC | AAGGCCCAGC | TATGGCCCCA | GGGTTGAAAA | GTTATGAGGG | TCAGGGGTCT | 60 |
| TTTGTGTCCG | GGTCTGGCTT | GGCTTTGTGT | CCGCGAGTTT | TTGTTCCGCT | CCGCAGCGCT | 120 |
| CTTCCCGGGC | AGGAGCCGTG | AGGCTCGGAG | GCGGCAGCGC | GGTCCCCGGC | CAGGAGCAAG | 180 |
| CGCCGGCCG | TGAGCGGCGG | CGGCAAAGGC | TGTGGGGAGG | GGGCTTCGCA | GATCCCCGAG | 240 |
| ATGCCGGAGT | TCCTGGAAGA | CCCCTCGGTC | CTGACAAAAG | ACAAGTTGAA | GAGTGAGTTG | 300 |
| GTCGCCAACA | ATGTGACGCT | GCCGGCCGGG | GAGCAGCGCA | AGACGTGTA | CGTCCAGCTC | 360 |

| | | | | | | |
|---|---|---|---|---|---|---|
| TACCTGCAGC | ACCTCACGGC | TCGCAACCGG | CCGCCGCTCC | CCGCCGGCAC | CAACAGCAAG | 420 |
| GGGCCCCCGG | ACTTCTCCAG | TGACGAAGAG | CGCGAGCCCA | CCCCGGTCCT | CGGCTCTGGG | 480 |
| GCCGCCGCCG | CGGGCCGGAG | CCGAGCAGCC | GTCGGCAGGA | AAGCCACAAA | AAAAACTGAT | 540 |
| AAACCCAGAC | AAGAAGATAA | AGATGATCTA | GATGTAACAG | AGCTCACTAA | TGAAGATCTT | 600 |
| TTGGATCAGC | TTGTGAAATA | CGGAGTGAAT | CCTGGTCCTA | TTGTGGGAAC | AACCAGGAAG | 660 |
| CTATATGAGA | AAAAGCTTTT | GAAACTGAGG | GAACAAGGAA | CAGAATCAAG | ATCTTCTACT | 720 |
| CCTCTGCCAA | CAATTTCTTC | TTCAGCAGAA | AATACAAGGC | AGAATGGAAG | TAATGATTCT | 780 |
| GACAGATACA | GTGACAATGA | AGAAGACTCT | AAAATAGAGC | TYAAGCTTGA | GAAGAGAGAA | 840 |
| CCACTAAAGG | GCAGAGCAAA | GACTCCAGTA | ACACTCAAGC | AAAGAAGAGT | TGAGCACAAT | 900 |
| CAGGTGGGAG | AAAAAACAGA | GGAAAGAAGA | GTAGAAAGGG | ATATTCTTAA | GGAAATGTTC | 960 |
| CCCTATGAAG | CATCTACACC | AACAGGAATT | AGTGCTAGTT | GCCGCAGACC | AATCAAAGGG | 1020 |
| GCTGCAGGCC | GGCCATTAGA | ACTCAGTGAT | TTCAGGATGG | AGGAGTCTTT | TTCATCTAAA | 1080 |
| TATGTTCCTA | AGTATGTTCC | CTTGGCAGAT | GTCAAGTCAG | AAAAGACAAA | AAAGGGACGC | 1140 |
| TCCATTCCCG | TATGGATAAA | AATTTGCTG | TTTGTTGTTG | TGGCAGTTTT | TTTGTTTTG | 1200 |
| GTCTATCAAG | CTATGGAAAC | CAACCAAGTA | AATCCCTTCT | CTAATTTTCT | TCATGTTGAC | 1260 |
| CCTAGAAAAT | CCAACTGAAT | GGTATCTCTT | TGGCACGTTC | AACTTGGTCT | CCTATTTCA | 1320 |
| ATAACTGTTG | AAAAACATTT | GTGTACACTT | GTTGACTCCA | AGAACTAAAA | ATAATGTGAT | 1380 |
| TTCGCCTCAA | TAAATGTAGT | ATTTCATTGA | AAAGCAAACA | AATATATAT | AAATGGACTT | 1440 |
| CATTAAAATG | TTTTTGAACT | TTGGACTAGT | AGGAGATCAC | TTTGTGCCAT | ATGAATAATC | 1500 |
| TTTTTTAGCT | CTGGAACTTT | TTGTAGGCTT | TATTTTTTA | ATGTGGGCAT | CTTATTTCAT | 1560 |
| TTTTGAAAAA | ATGTATATGT | TTTTTGTGTA | TTTGGGAAAC | GAAGGGTGAA | ACATGGTAGT | 1620 |
| ATAATGTGAA | GCTACACATT | TAAATACTTA | GAATTCTTAC | AGAAAAGATT | TTAAGAATTA | 1680 |
| TTCTCTGCTG | AATAAAAACT | GCAAATATGT | GAAACATAAT | GAAATTCAGT | AAGAGGAAAA | 1740 |
| GTAACTTGGT | TGTACTTTTT | GTAACTGCAA | CAAAGTTTGA | TGGTGTTTAT | GAGGAAAAGT | 1800 |
| ACAGCAATAA | TCTCTTCTGT | AACCTTTATT | AATAGTAATG | TTGTTGTAGC | CCTATCATAC | 1860 |
| TCACTTTTTA | AGACACAGTA | TCATGAAAGT | CCTATTTCAG | TAAGACCCAT | TTACATACAG | 1920 |
| TAGATTTTTA | GCAGAGATCT | TTTAGTGTAA | CATACATATT | TTAGAGAATT | GTTGGCTAGC | 1980 |
| TGTACATGTT | TTGAAAAGCT | GTTTAGCTAG | CTATAAGGCT | ATAATTGGAA | ATTTGTATTT | 2040 |
| TTTATTTACA | GCAAACATT | TATTCAGTCA | TCCAGTTTGC | TACCAAAATA | TGTTTAGAT | 2100 |
| AAGTGTGTGT | ATGTTTGTTT | AGAAGTTAGA | AATTGTAAAC | ACTGGTCTTA | TGTTTCATTT | 2160 |
| GGATTCATTA | TTGCATTGTC | TTGTTACCAG | AAACAAATTT | TGCCGAGCTT | TTTTTGCCCT | 2220 |
| ATATTTCCCA | GCATAATTTG | ATTAGAAAGT | ACAAAAGGG | CCGGGCGCGG | TGGCTTACGC | 2280 |
| CTGTAATCCC | AGCACTTTGG | GAGGCCAGGG | CGGGTGGATC | ACGAGGTCAG | GAGATCGGGA | 2340 |
| CCATCCTGGC | CAACATGGTG | AAACCCCGTC | TCTACTAAAA | AAAAAAAAA | AA | 2392 |

( 2 ) INFORMATION FOR SEQ ID NO:6:

( i ) SEQUENCE CHARACTERISTICS:
        ( A ) LENGTH: 345 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

| Met<br>1 | Pro | Glu | Phe | Leu<br>5 | Glu | Asp | Pro | Ser | Val<br>10 | Leu | Thr | Lys | Asp | Lys<br>15 | Leu |
| --- | --- | --- | --- | --- | --- | --- | --- | --- | --- | --- | --- | --- | --- | --- | --- |
| Lys | Ser | Glu | Leu<br>20 | Val | Ala | Asn | Asn | Val<br>25 | Thr | Leu | Pro | Ala | Gly<br>30 | Glu | Gln |
| Arg | Lys | Asp<br>35 | Val | Tyr | Val | Gln | Leu<br>40 | Tyr | Leu | Gln | His | Leu<br>45 | Thr | Ala | Arg |
| Asn | Arg<br>50 | Pro | Pro | Leu | Pro | Ala<br>55 | Gly | Thr | Asn | Ser | Lys<br>60 | Gly | Pro | Pro | Asp |
| Phe<br>65 | Ser | Ser | Asp | Glu | Glu<br>70 | Arg | Glu | Pro | Thr | Pro<br>75 | Val | Leu | Gly | Ser | Gly<br>80 |
| Ala | Ala | Ala | Ala | Gly<br>85 | Arg | Ser | Arg | Ala | Ala<br>90 | Val | Gly | Arg | Lys | Ala<br>95 | Thr |
| Lys | Lys | Thr | Asp<br>100 | Lys | Pro | Arg | Gln | Glu<br>105 | Asp | Lys | Asp | Asp | Leu<br>110 | Asp | Val |
| Thr | Glu | Leu<br>115 | Thr | Asn | Glu | Asp | Leu<br>120 | Leu | Asp | Gln | Leu | Val<br>125 | Lys | Tyr | Gly |
| Val | Asn<br>130 | Pro | Gly | Pro | Ile<br>135 | Val | Gly | Thr | Thr | Arg<br>140 | Lys | Leu | Tyr | Glu | Lys |
| Lys<br>145 | Leu | Leu | Lys | Leu | Arg<br>150 | Glu | Gln | Gly | Thr | Glu<br>155 | Ser | Arg | Ser | Ser | Thr<br>160 |
| Pro | Leu | Pro | Thr | Ile<br>165 | Ser | Ser | Ser | Ala | Glu<br>170 | Asn | Thr | Arg | Gln | Asn<br>175 | Gly |
| Ser | Asn | Asp | Ser<br>180 | Asp | Arg | Tyr | Ser | Asp<br>185 | Asn | Glu | Glu | Asp | Ser<br>190 | Lys | Ile |
| Glu | Leu | Lys<br>195 | Leu | Glu | Lys | Arg | Glu<br>200 | Pro | Leu | Lys | Gly | Arg<br>205 | Ala | Lys | Thr |
| Pro | Val<br>210 | Thr | Leu | Lys | Gln | Arg<br>215 | Arg | Val | Glu | His | Asn<br>220 | Gln | Val | Gly | Glu |
| Lys<br>225 | Thr | Glu | Glu | Arg | Arg<br>230 | Val | Glu | Arg | Asp | Ile<br>235 | Leu | Lys | Glu | Met | Phe<br>240 |
| Pro | Tyr | Glu | Ala | Ser<br>245 | Thr | Pro | Thr | Gly | Ile<br>250 | Ser | Ala | Ser | Cys | Arg<br>255 | Arg |
| Pro | Ile | Lys | Gly<br>260 | Ala | Ala | Gly | Arg | Pro<br>265 | Leu | Glu | Leu | Ser | Asp<br>270 | Phe | Arg |
| Met | Glu | Glu<br>275 | Ser | Phe | Ser | Ser | Lys<br>280 | Tyr | Val | Pro | Lys | Tyr<br>285 | Val | Pro | Leu |
| Ala | Asp<br>290 | Val | Lys | Ser | Glu | Lys<br>295 | Thr | Lys | Lys | Gly | Arg<br>300 | Ser | Ile | Pro | Val |
| Trp<br>305 | Ile | Lys | Ile | Leu | Leu<br>310 | Phe | Val | Val | Val | Ala<br>315 | Val | Phe | Leu | Phe | Leu<br>320 |
| Val | Tyr | Gln | Ala | Met<br>325 | Glu | Thr | Asn | Gln | Val<br>330 | Asn | Pro | Phe | Ser | Asn<br>335 | Phe |
| Leu | His | Val | Asp<br>340 | Pro | Arg | Lys | Ser | Asn<br>345 | | | | | | | |

( 2 ) INFORMATION FOR SEQ ID NO:7:

( i ) SEQUENCE CHARACTERISTICS:
        ( A ) LENGTH: 52 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:7:

| Pro<br>1 | Glu | Phe | Leu | Glu<br>5 | Asp | Pro | Ser | Val | Leu<br>10 | Thr | Lys | Asp | Lys | Leu<br>15 | Lys |
| --- | --- | --- | --- | --- | --- | --- | --- | --- | --- | --- | --- | --- | --- | --- | --- |

| | | | | | | | | | | | | | | |
|---|---|---|---|---|---|---|---|---|---|---|---|---|---|---|
| Ser | Glu | Leu | Val<br>20 | Ala | Asn | Asn | Val | Thr<br>25 | Leu | Pro | Ala | Gly | Glu<br>30 | Gln | Arg |
| Lys | Asp | Val<br>35 | Tyr | Val | Gln | Leu | Tyr<br>40 | Leu | Gln | His | Leu | Thr<br>45 | Ala | Arg | Asn |
| Arg | Pro<br>50 | Pro | Leu | | | | | | | | | | | | |

What is claimed is:

1. A method for measuring total thymopoietin levels in a human serum or plasma sample comprising dissociating by acidification thymopoietin (TP) from its association with any complexing protein with which it is bound, and releasing said bound TP into said sample in a unbound state;

extracting said unbound TP from association with any interfering substances;

preparing a sample of said TP for a selected assay format by removing contaminating solvents and reagents incompatible with said assay format; and measuring said TP in said assay.

2. The method according to claim 1 wherein said dissociating step comprises acidifying said sample to a pH of about 3.

3. The method according to claim 1 further comprising adding reagents to prevent non-specific binding in said dissociating step and in said remaining steps.

4. The method according to claim 1 wherein in said dissociating step, said sample is incubated for about 1 hour at room temperature.

5. The method according to claim 1 wherein said extraction step comprises subjecting said sample to reverse phase column chromatography.

6. The method according to claim 1 wherein said preparing step comprises evaporation and lyophilization of said sample.

7. The method according to claim 1 wherein said measuring step is performed by immunoassay.

8. The method according to claim 7 wherein said immunoassay is a displacement radioimmunoassay which generates a total sample TP displacement curve which is parallel to a standard TP displacement curve.

9. The method according to claim 7 wherein said immunoassay is a sandwich ELISA immunoassay which generates a total sample TP binding curve which is parallel to a standard TP binding curve.

10. A kit useful in measuring levels of thymopoietin in a human serum or plasma sample comprising a plate coated with an antibody which specifically binds thymopoietin, a detectably labelled antibody which binds thymopoietin, an acidification reagent which dissociates thymopoietin from association with any complexing protein with which it is bound, a standard, and a suitable diluent.

11. The kit according to claim 10 wherein said standard is synthetic thymopoietin 1–52 SEQ ID NO: 7.

* * * * *